US012667310B2

(12) United States Patent
Kirszenblat et al.

(10) Patent No.: US 12,667,310 B2
(45) Date of Patent: Jun. 30, 2026

(54) EVALUATION METHOD OF A CONTACT PRESSURE BETWEEN AN OPTICAL SENSOR AND THE SKIN OF A USER AND ASSOCIATED DEVICE

(71) Applicant: WITHINGS, Issy les Moulineaux (FR)

(72) Inventors: Romain Kirszenblat, Issy les Moulineaux (FR); Paul Edouard, Issy les Moulineaux (FR)

(73) Assignee: WITHINGS, Issy les Moulineaux (FR)

( * ) Notice: Subject to any disclaimer, the term of this patent is extended or adjusted under 35 U.S.C. 154(b) by 0 days.

(21) Appl. No.: 18/859,040

(22) PCT Filed: Apr. 12, 2023

(86) PCT No.: PCT/EP2023/059588
§ 371 (c)(1),
(2) Date: Oct. 22, 2024

(87) PCT Pub. No.: WO2023/208586
PCT Pub. Date: Nov. 2, 2023

(65) Prior Publication Data
US 2025/0288252 A1 Sep. 18, 2025

(30) Foreign Application Priority Data
Apr. 25, 2022 (FR) ...................................... 2203817

(51) Int. Cl.
*A61B 5/00* (2006.01)
*A61B 5/024* (2006.01)

(52) U.S. Cl.
CPC ........ *A61B 5/6843* (2013.01); *A61B 5/02433* (2013.01); *A61B 5/6826* (2013.01); *A61B 5/7246* (2013.01); *A61B 5/681* (2013.01)

(58) Field of Classification Search
CPC . A61B 5/6843; A61B 5/7246; A61B 5/02416; A61B 5/02125
See application file for complete search history.

(56) References Cited

U.S. PATENT DOCUMENTS 9,408,541 B2 * 8/2016 Kuri ................... A61B 5/02007
10,456,046 B2 * 10/2019 Eagle ................. A61B 5/02152
(Continued)

FOREIGN PATENT DOCUMENTS

CN 113827185 A 12/2021
CN 114343596 A 4/2022
(Continued)

OTHER PUBLICATIONS

International Search Report as issued in International Patent Application No. PCT/EP2023/059588, dated Jul. 13, 2023.
(Continued)

*Primary Examiner* — Oommen Jacob
(74) *Attorney, Agent, or Firm* — CUSHMAN PARTNERS, LLC

(57) ABSTRACT
An evaluation method of a contact pressure between an optical sensor and a skin of a user, the method including a) determination of first optical data, using a first optical signal obtained by the optical sensor at a first wavelength, b) determination of second optical data, using a second optical signal obtained by the optical sensor at a second wavelength, different from the first wavelength, c) analysis of at least one comparison of the first optical data with the second optical data, the analysis generating information relating to the contact pressure between the optical sensor and the skin.

23 Claims, 13 Drawing Sheets

1000

(56)                    References Cited

U.S. PATENT DOCUMENTS

Figure 1:
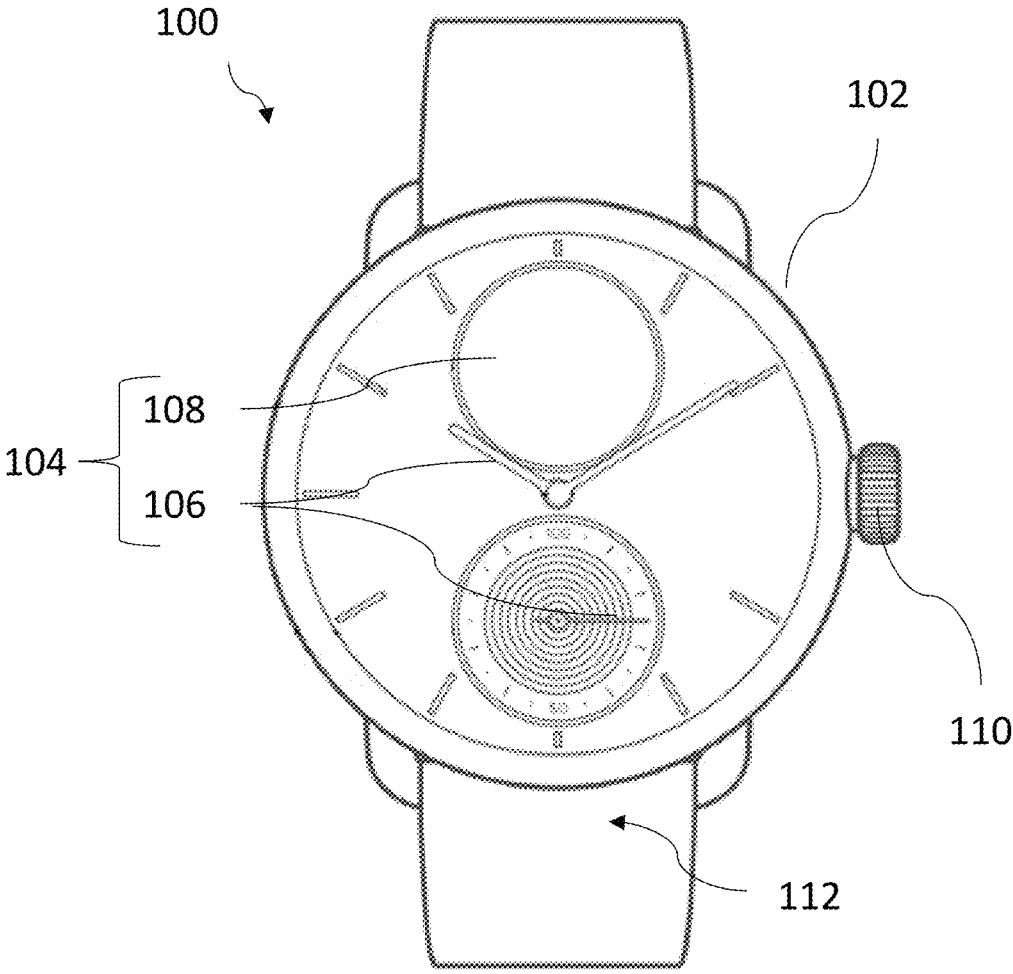

| | | | | |
|---|---|---|---|---|
| 10,874,348 | B1 * | 12/2020 | Han | A61B 5/6843 |
| 11,850,071 | B1 * | 12/2023 | Coakley | A61B 5/332 |
| 11,937,923 | B2 * | 3/2024 | Edouard | A61B 5/14552 |
| 12,336,844 | B2 * | 6/2025 | Morgan | A61B 5/02416 |
| 2010/0324384 | A1 * | 12/2010 | Moon | A61B 5/14552 600/595 |
| 2012/0016210 | A1 | 1/2012 | Kim et al. | |
| 2012/0190944 | A1 * | 7/2012 | Thaveeprungsriporn | A61B 5/1455 600/310 |
| 2013/0184594 | A1 * | 7/2013 | Shelley | A61B 5/7246 600/490 |
| 2013/0296665 | A1 * | 11/2013 | Kassim | A61B 5/0295 600/310 |
| 2013/0296666 | A1 * | 11/2013 | Kumar | A61B 5/02416 600/310 |
| 2014/0018648 | A1 * | 1/2014 | Pao | A61B 5/14552 600/364 |
| 2014/0276149 | A1 | 9/2014 | Takahashi et al. | |
| 2017/0188854 | A1 * | 7/2017 | Banet | A61B 5/0022 |
| 2017/0209053 | A1 | 7/2017 | Pantelopoulos et al. | |
| 2019/0387985 | A1 * | 12/2019 | Kang | A61B 5/6843 |
| 2020/0146629 | A1 | 5/2020 | Sun et al. | |
| 2020/0146630 | A1 | 5/2020 | Joe et al. | |
| 2021/0251571 | A1 * | 8/2021 | Morgan | D04B 1/16 |
| 2023/0270386 | A1 * | 8/2023 | Corona Aparicio | A61B 5/1118 600/595 |
| 2025/0288252 | A1 * | 9/2025 | Kirszenblat | A61B 5/6826 |

FOREIGN PATENT DOCUMENTS

| | | |
|---|---|---|
| EP | 3 903 677 A1 | 11/2021 |
| JP | 2013-183845 A | 9/2013 |

OTHER PUBLICATIONS

Geun, E., et al., "Measurement Site and Applied Pressure Consideration in Wrist Photoplethysmography," The 23rd International Technical Conference on Circuits/Systems, Computers and Communications), (Year: 2008), pp. 1129-1132.

Chen, S.-H., et al., "Development of a Portable All-Wavelength PPG Sensing Device for Robust Adaptive-Depth Measurement: A Spectrometer Approach with a Hydrostatic Measurement Example," Sensors (DOI: 10.3390/s20226556), (Year: 2020), 12 pages.

Cao, Y., et al., "Crisp-BP continuous wrist PPG-based blood pressure measurement," Proceedings of the 27th Annual International Conference on Mobile Computing and Networking, Oct. 2021, pp. 378-391, XP058751428, DOI: 10.1145/3447993.3483241 ISBN: 978-1-4503-8342-4.

* cited by examiner

500

600

EVALUATION METHOD OF A CONTACT PRESSURE BETWEEN AN OPTICAL SENSOR AND THE SKIN OF A USER AND ASSOCIATED DEVICE

CROSS-REFERENCE TO RELATED APPLICATIONS

This application is the U.S. National Stage of PCT/EP2023/059588, filed Apr. 12, 2023, which in turn claims priority to French patent application number 2203817 filed Apr. 25, 2022. The content of these applications are incorporated herein by reference in their entireties.

The present description relates to devices and associated methods for measuring a pulsatile optical signal, i.e. for optically measuring a quantity modulated or influenced by an individual's heartbeat. Examples include signals used in photoplethysmography (or "PPG", the corresponding signals being referred to hereinafter as PPG) methods. In particular, the present description concerns the positioning of a portable device comprising an optical sensor (e.g. a PPG sensor), and in particular concerns the clamping of the device against the skin of a user. One application is wearable devices, such as watches or connected trackers with optical sensors.

State of the Art

When incorrectly positioned, a PPG sensor generates a poor-quality measurement of blood flow pulsatility. Positioning at the wrist is a further source of difficulty, as it imposes a PPG measurement in reflection and not in transmission, as do most finger devices. Among the parameters affecting measurement, the contact pressure between the PPG sensor and the skin has been studied (see in particular "*Measurement Site and Applied Pressure Consideration in Wrist Photoplethysmography*", by Geun et al. in *The 23rd International Technical Conference on Circuits/Systems, Computers and Communications*) and solutions have been proposed.

For example, US2017/0209053 (Fitbit Inc.) proposes a method using the quality of the PPG signal to signal the user to tighten the device more on the wrist. Examples of poor positioning include the situation where the PPG sensor presses too hard against the skin and generates a poor-quality measurement. Methods exist to inform the user of excessive contact pressure. For example, document U.S. Pat. No. 10,874,348 (Apple Inc.) proposes a method with a dedicated force sensor. For example, US2020/0146629 (Huawei) proposes a method consisting in calibrating the sensor by taking PPG measurements at different clamping settings. For example, document US2020/0146630 (Samsung Electronics Co) proposes a method using a PPG measurement to determine the clamping condition using the AC/DC ratio at a given wavelength; in particular, this document proposes to use this AC/DC ratio at several given wavelengths (in the green, blue, red, infrared, etc. range). For example, document CN113827185 (Huawei) also proposes to analyze the PPG signal to determine a degree of tightness. US2019/0387985 uses a multi-wave-length signal to obtain a contact pressure between the body and the sensor.

Each of these solutions presents functional or technical difficulties: integration of additional equipment into a wearable device (usually on the wrist), calibration required for each user, imprecision of algorithms, dependence on conditions of use (temperature, time of day, etc.).

SUMMARY OF THE INVENTION

An aim of the present description is to propose methods and associated devices or systems that do not present at least one of the aforementioned difficulties. More specifically, the methods and devices of the present description make use of one or more optical signals, for example PPG signals. In particular, according to one aspect of the description, optical data obtained from optical signals at different wavelengths are compared with each other, the result of this comparison being compared with a threshold; according to another aspect of the description, optical data obtained from optical signals transmitted in the green and red range or in the green and infrared range are combined; according to another aspect of the description, optical data obtained from optical signals generated by differently spaced light source/receiver pairs are compared.

The invention is defined by the claims.

In an embodiment, a method of evaluating a contact pressure between an optical sensor and a skin of a user is proposed, the method comprising: a) determination of first optical data, using a first optical signal obtained by the optical sensor at a first wave-length; b) determination of second optical data, using a second optical signal obtained by the optical sensor at a second wavelength, different from the first wavelength; c) analysis of at least one comparison of the first optical data and the second optical data, the analysis generating information relating to the contact pressure between the optical sensor and the skin. The optical signals may be heartbeat-modulated optical signals. In this case, more specifically, the optical data comprise information relating to the pulsatile component of the optical signal. For example, determination of the optical data may comprise processing involving extraction of pulsatile data from the optical signal. The method may further comprise: depending at least on the result of the analysis, generating notification instructions to the user, the notification prompting the user to modify, in particular to decrease, the contact pressure between the skin and the measuring device.

The comparison may be carried out by calculating a parameter, the parameter being calculated from the first optical data and the second optical data. The parameter is used to deduce information about the contact pressure between the optical sensor and the skin. In particular, the value of the parameter may be representative of the contact pressure between the optical sensor and the skin. Complementary or alternative to generating instructions, the method may include storing the value of the parameter.

The calculation of the parameter may comprise the calculation of a ratio between the first optical data and the second optical data, so that the comparison is made by means of a ratio. Alternatively or additionally, the parameter calculation may involve calculating a difference between the first optical data and the second optical data, so that the comparison involves subtraction or subtraction with division (to normalize).

The analysis may involve comparing the parameter value with a threshold (i.e. the parameter is compared with a threshold). In this case, instructions may be generated in response to the comparison (for example, if the parameter value is below or above the threshold). In particular, the threshold may be set according to the characteristics of the optical sensor and the wavelengths used. The threshold may be between 0.5 and 10, for example between 0.5 and 2.

The first wavelength may be less than 600 nm and the second wavelength may be strictly greater than 600 nm, or even greater than 650 nm.

The first wavelength may be between 400 nm and 600 nm and the second wavelength may be between 600 nm and 1000 nm.

The difference between the first wavelength and the second wavelength may be at least 50 nm.

The first wavelength may be less than 540 nm and the second wavelength may be greater than 650 nm or greater than 800 nm.

The first wavelength may be between 480 and 540 nm and the second wave-length may be between 650 and 665 nm.

The evaluation method may comprise a step of determining third optical data, using a third optical signal obtained by the optical sensor at a third wavelength, different from the first wavelength and the second wavelength, and the analysis comprises an analysis of the first optical data, the second optical data and the third optical data. In particular, the analysis may comprise analysis of a comparison of the first optical data with the second optical data and analysis of a comparison of the first optical data with the third optical data. In particular, both comparisons may be carried out by calculating two parameters, analogously to the comparison described above for a single parameter. The analysis may involve comparing the value of each of the parameters with a threshold. An identical threshold for both parameters may be used, or two thresholds (one for each parameter) may be used. The third length may be greater than 800 nm, and for example between 800 nm and 1000 nm, or for example between 920 nm and 960 nm.

The method may include a step of initiating an optical measurement using the optical sensor and a step of interrupting the optical measurement as a function of at least one result of the analysis, the analysis having generated information relating to the contact pressure between the optical sensor and the skin.

In one embodiment, an optical analysis method is proposed using an optical sensor configured to be in contact with a user's skin, the method comprising the following steps: a) determination of first optical data, using a first optical signal obtained by the optical sensor at a first wavelength below 600 nm; b) determination of second optical data, using a second optical signal obtained by the optical sensor at a second wavelength above 650 nm; c) analysis of a comparison of the first optical data and the second optical data, the analysis comprising a calculation of a parameter. In particular, the comparison may be performed by calculating a parameter from the first optical data and the second optical data. The calculation of the parameter may comprise (or even be) the calculation of a ratio between the first optical data and the second optical data (or the inverse ratio).

In an embodiment, a method of evaluating a contact pressure between an optical sensor and a user's skin is proposed, the method comprising: a) determination of first optical data, using a first optical signal obtained by the optical sensor at a first wavelength; b) determination of second optical data, using a second optical signal obtained by the optical sensor at a second wavelength; c) depending on the result of an analysis of at least one comparison of the first optical data and the second optical data, generating notification instructions for the user, the notification prompting the user to modify, in particular to reduce, the contact pressure between the skin and the measuring device.

In an embodiment, a method of evaluating a contact pressure between an optical sensor and a user's skin is proposed, the method comprising: a) determination of first optical data, using a first optical signal obtained by a first light source/receiver pair of the optical sensor, b) determination of second optical data, using a second optical signal obtained by a second light source/receiver pair of the optical sensor, the distance between the light source and the receiver of the second pair being greater than the distance between the light source and the receiver of the first pair, c) analysis of at least one comparison of the first optical data and the second optical data, the analysis generating information relating to the contact pressure between the optical sensor and the skin.

Similar to what has been described above, notification instructions may be generated. In the same way, analysis may be carried out by means of a parameter, as mentioned above.

In an embodiment, the optical sensor comprises a light source and two light receivers, the light receivers being arranged so that their respective distances from the light source are different. The light source and one of the light receivers form the first pair, and the light source and the other of the light receivers form the second pair.

In an embodiment, the optical sensor comprises two light sources and a light receiver, the light sources being arranged so that their respective distances from the light receiver are different. The light receiver and one of the light sources form the first pair, and the light receiver and the other of the light sources form the second pair.

In the methods described herein, the optical signals may be heartbeat-modulated optical signals, for example PPG photoplethysmography signals. The optical sensor may be a PPG sensor. The optical data may be determined using a perfusion index.

In an embodiment, it is proposed to use a comparison of optical data obtained at a wavelength below 600 nm (e.g. corresponding to green) on the one hand, and optical data obtained at a wavelength above 650 nm (e.g. corresponding to red or infrared) on the other hand, to assess the presence of blood in superficial tissues. The optical data may include a perfusion index. The comparison may be made by calculating a ratio. The value of the comparison (e.g. the value of the ratio of ratios) in particular may be compared with a threshold.

The methods described above may be implemented by control circuitry comprising a memory and a processor. Control circuitry may be part of a measuring device, such as a watch.

In an embodiment, a computer program product is provided comprising instructions which, when the program is executed by control circuitry, cause the latter to implement the steps of at least one of the methods described above.

In an embodiment, there is provided a measuring device comprising an optical sensor comprising a light source configured to generate light towards a user's skin and comprising a light receiver, configured to detect light from the user's skin (in use configuration), wherein the measuring device is configured to implement at least one method from those described above. The measuring device may comprise control circuitry with a processor, the processor being configured to implement at least one method from those described above.

The device may further comprise tightening means, fastening means or a wristband for holding the optical sensor against the user's skin. The notification to the user described above, when issued, includes an indication inviting the user to modify the tightening of the wristband, and in particular to loosen it. The measuring device may include a user interface configured to notify the user of the notification.

When too much pressure is exerted on the skin where the optical measurement is taken, the most superficial blood vessels experience blood reflux, with the blood present in these vessels being partially or totally expelled. As a result, an optical signal obtained at a wavelength that penetrates the deepest into the skin will undergo a slight change, and the optical signal obtained at a wavelength that penetrates the least deeply into the skin will undergo a more significant change. In terms of pulsatility, this translates into a lower normalized pulsatile amplitude (known as the perfusion index or simply perfusion). Similarly, the optical signal most modulated by blood hemoglobin will undergo a more significant change, and the optical signal least modulated by hemoglobin will undergo a weaker change. The effects of penetration depth and hemoglobin absorption are cumulative, particularly for wavelength pairs corresponding to green and red, or green and infrared. For example, wavelengths corresponding to green are more strongly absorbed by hemoglobin and penetrate little into the skin: as a result, the perfusion index of green decreases sharply when the contact pressure between an optical sensor and the skin is high. Conversely, wavelengths corresponding to red or infrared are less strongly absorbed by hemoglobin and penetrate deep into the skin, so the perfusion index for red or infrared is little affected by the contact pressure between the optical sensor and the skin.

The measuring device processes the optical signals to generate optical data relating respectively to the two different wavelengths, and compares these data. In particular, the measuring device generates perfusion indices and calculates a "ratio of ratios", which may be the ratio of the green perfusion index to the red (or infrared) perfusion index. By normalizing the green perfusion index, which varies greatly as a function of contact pressure, with the red perfusion index, which varies very little, it is possible to avoid external factors that may disrupt optical signals: temperature, positioning of the optical sensor, skin color, hairiness, tension, drop in blood circulation, ambient luminosity, and so on. External factors are those that do not depend on the contact pressure between the optical sensor and the skin.

Moreover, by combining the effect of the greater absorption of green with its shallower depth, the variation in the green perfusion index is all the greater, enabling the measuring device, after normalization with the red perfusion index, to discriminate contact pressure levels without calibration on the user. This makes the method even more robust.

PRESENTATION OF FIGURES

Figure 2:
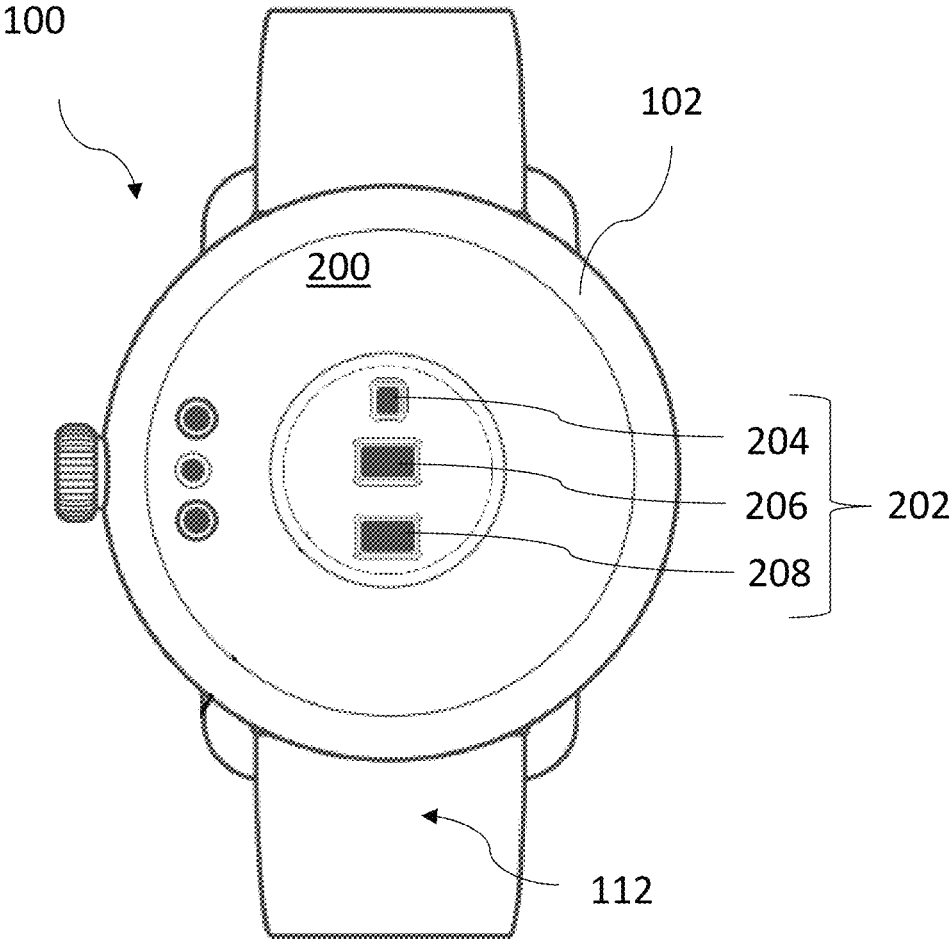
Figure 3:
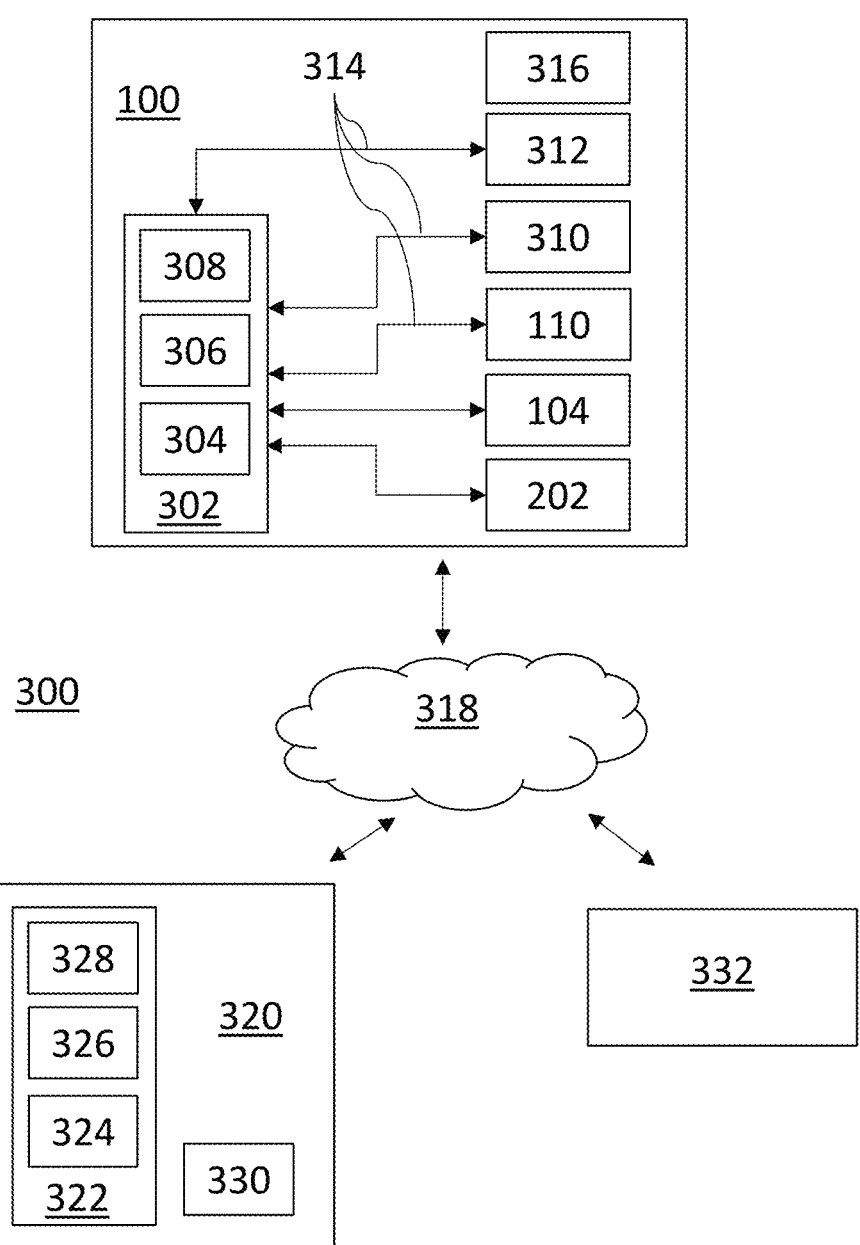
Figure 4:
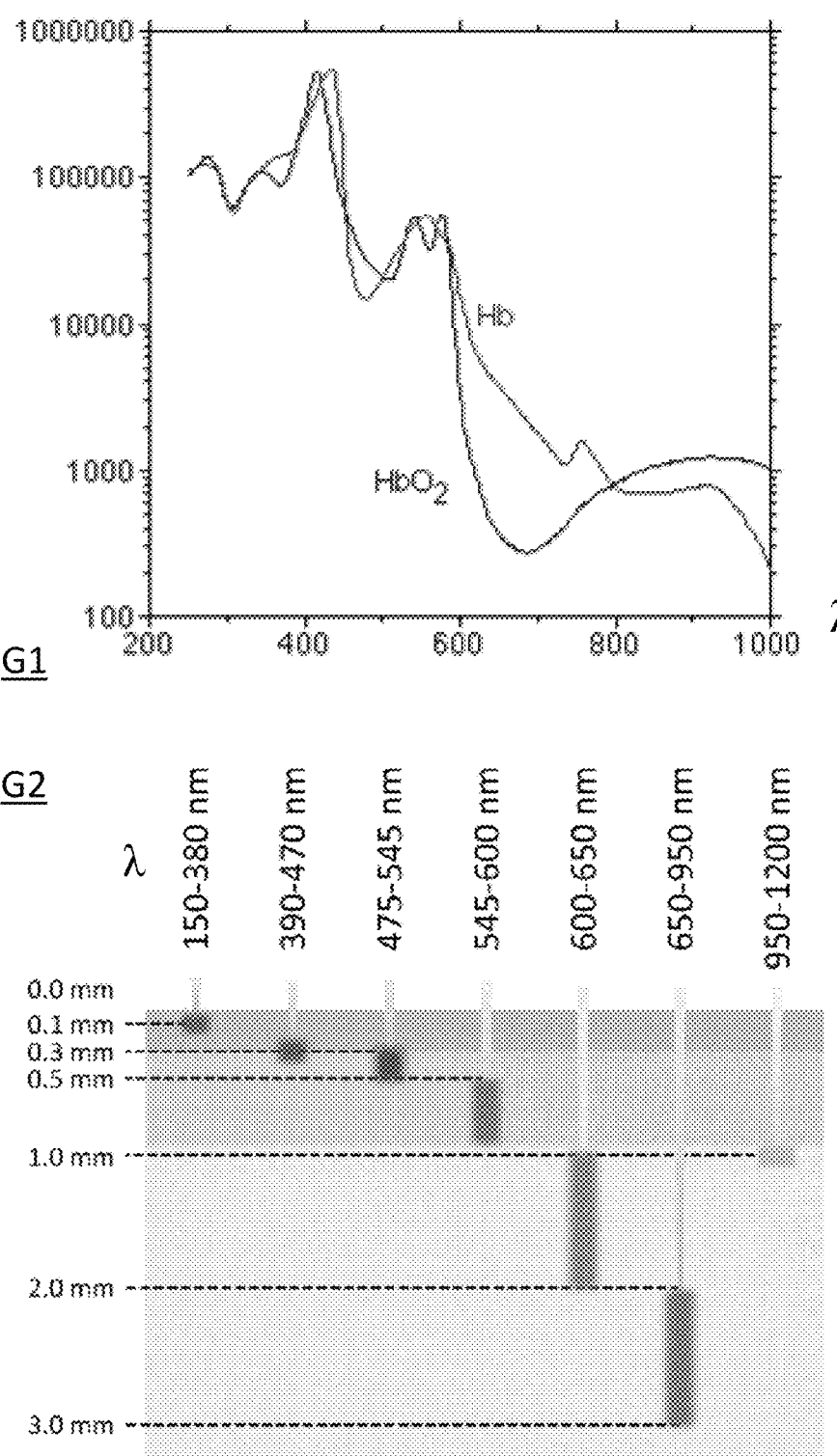
Figure 5:
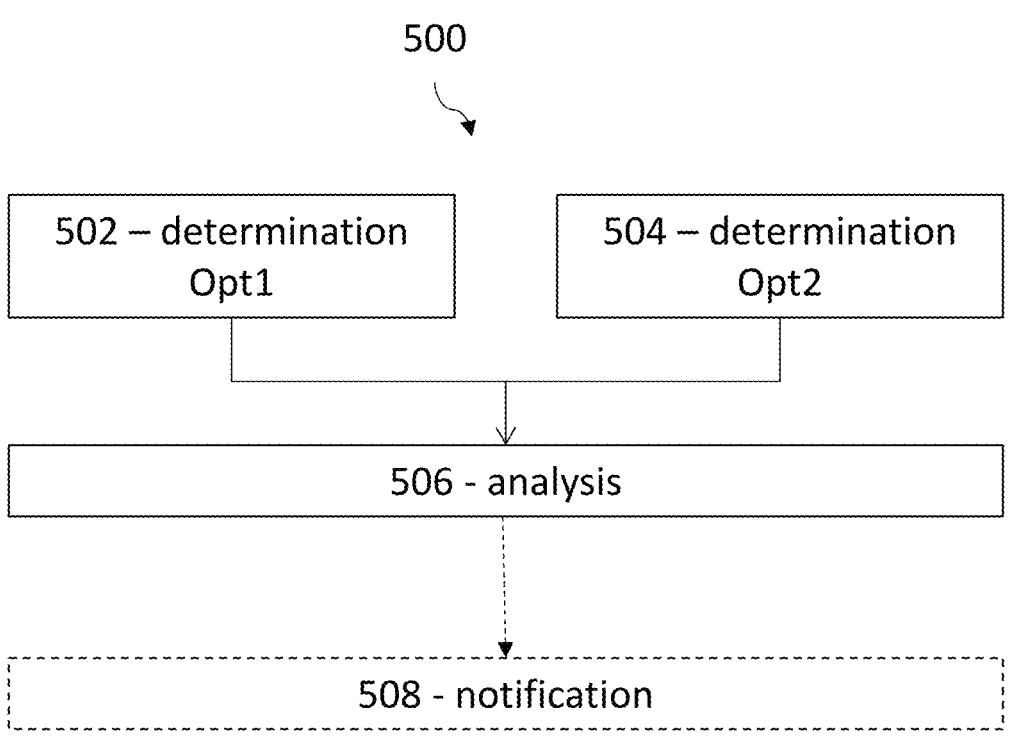
Figure 6:
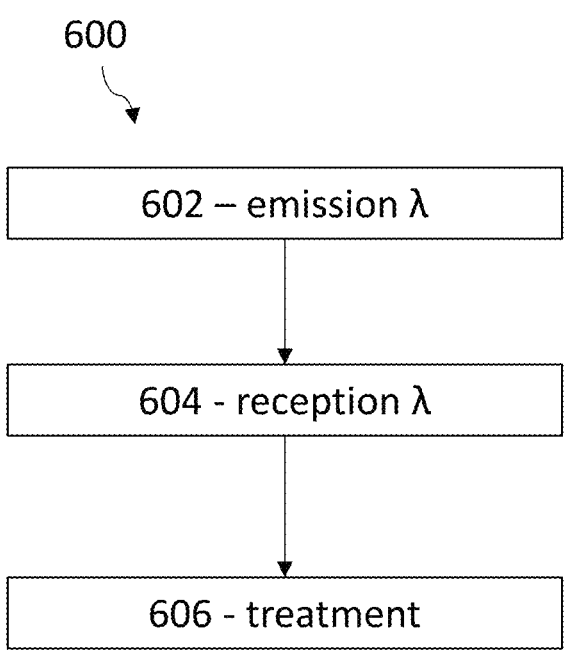
Figure 7:
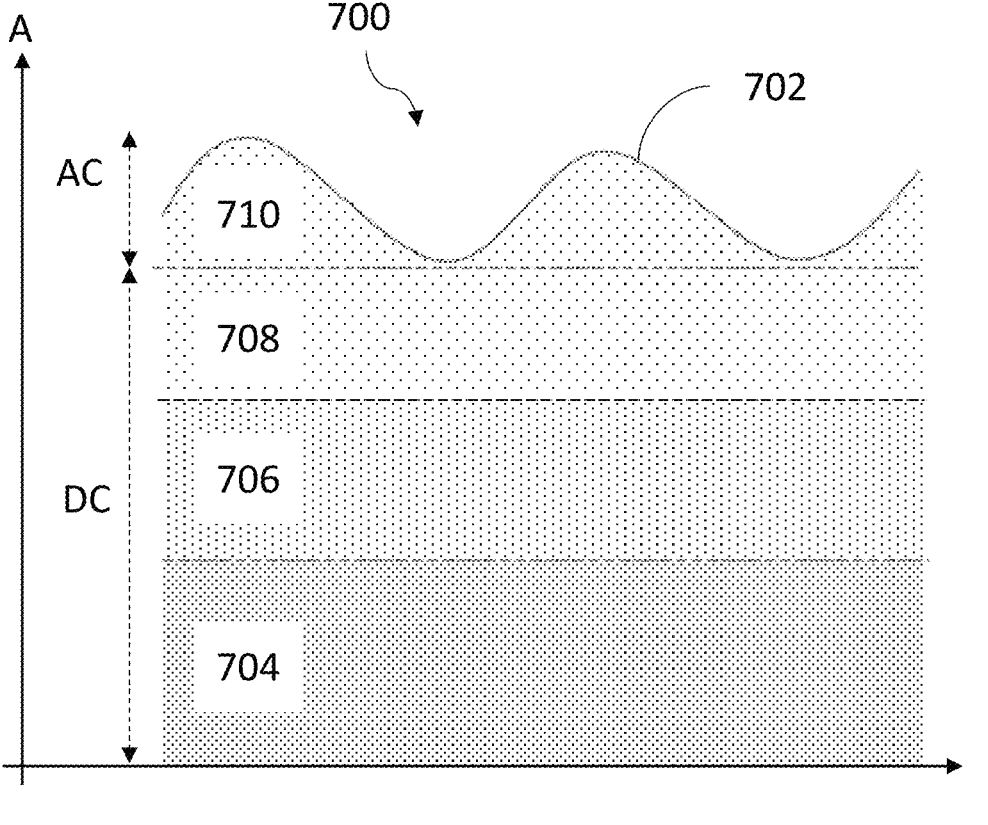
Figure 8:
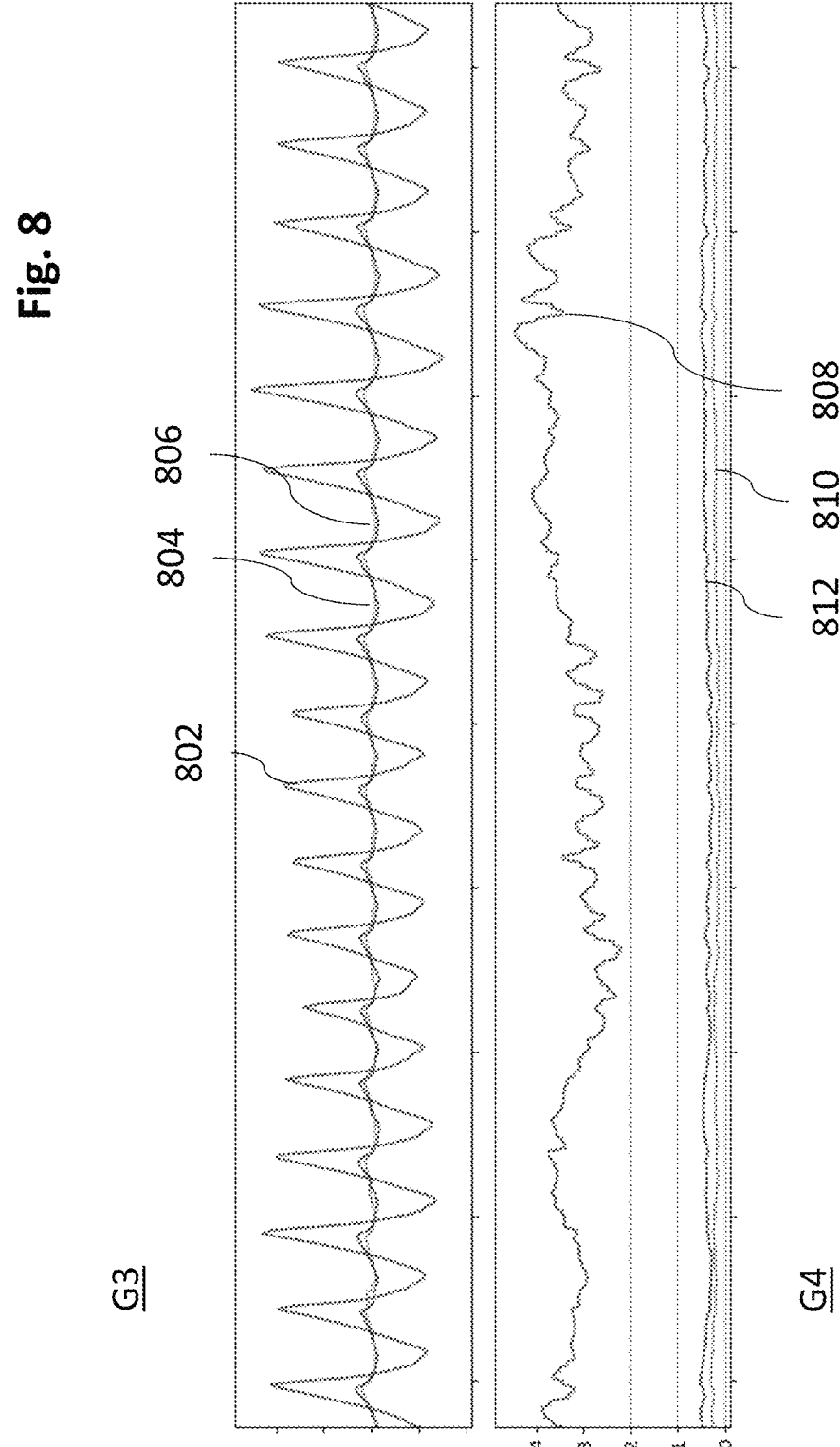
Figure 9:
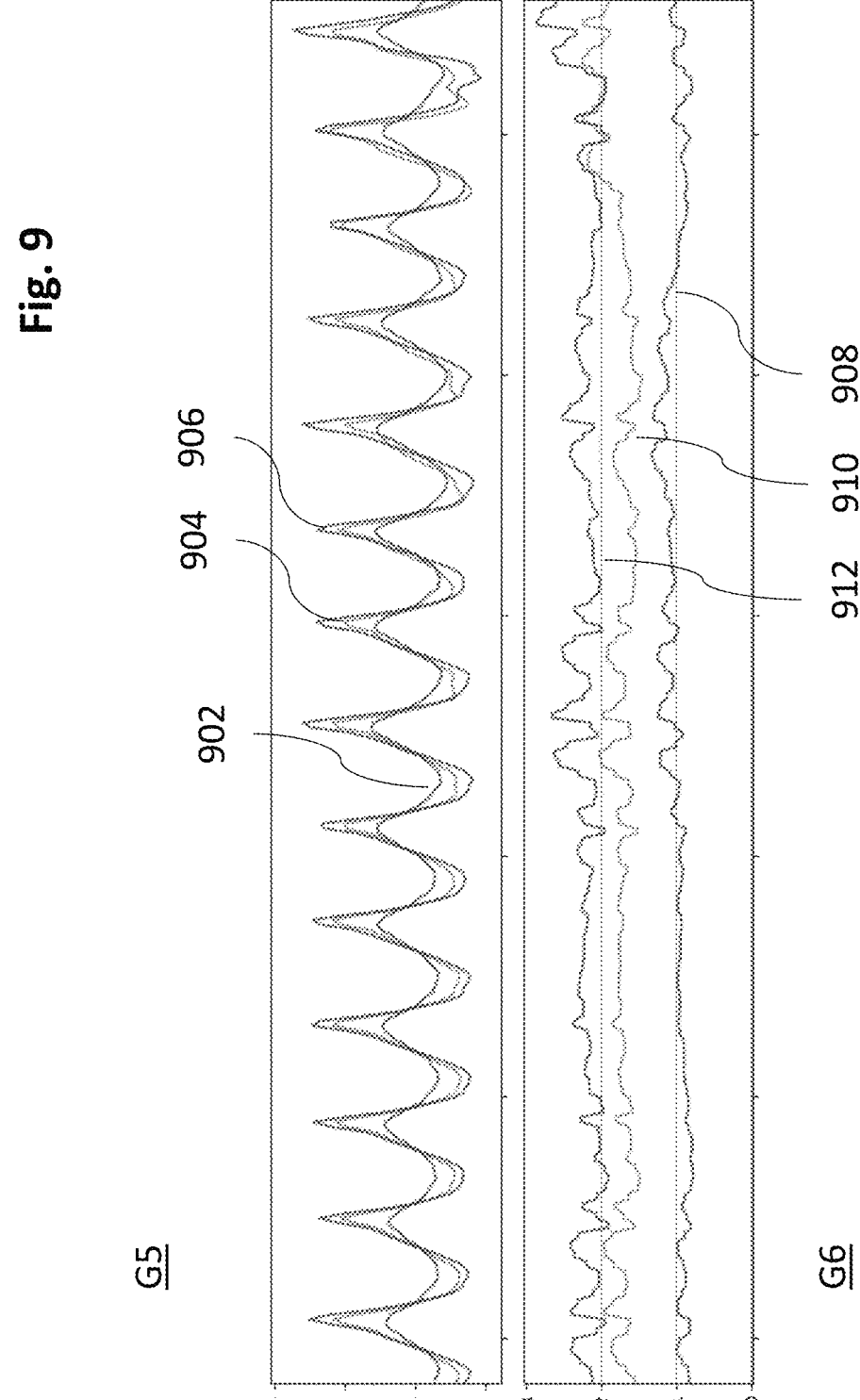
Figure 10:
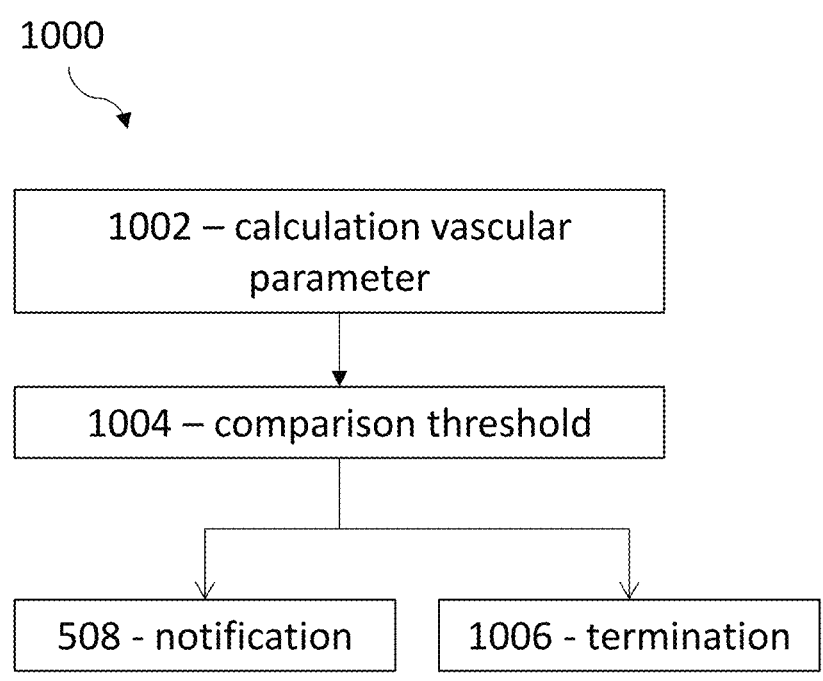
Figure 11:
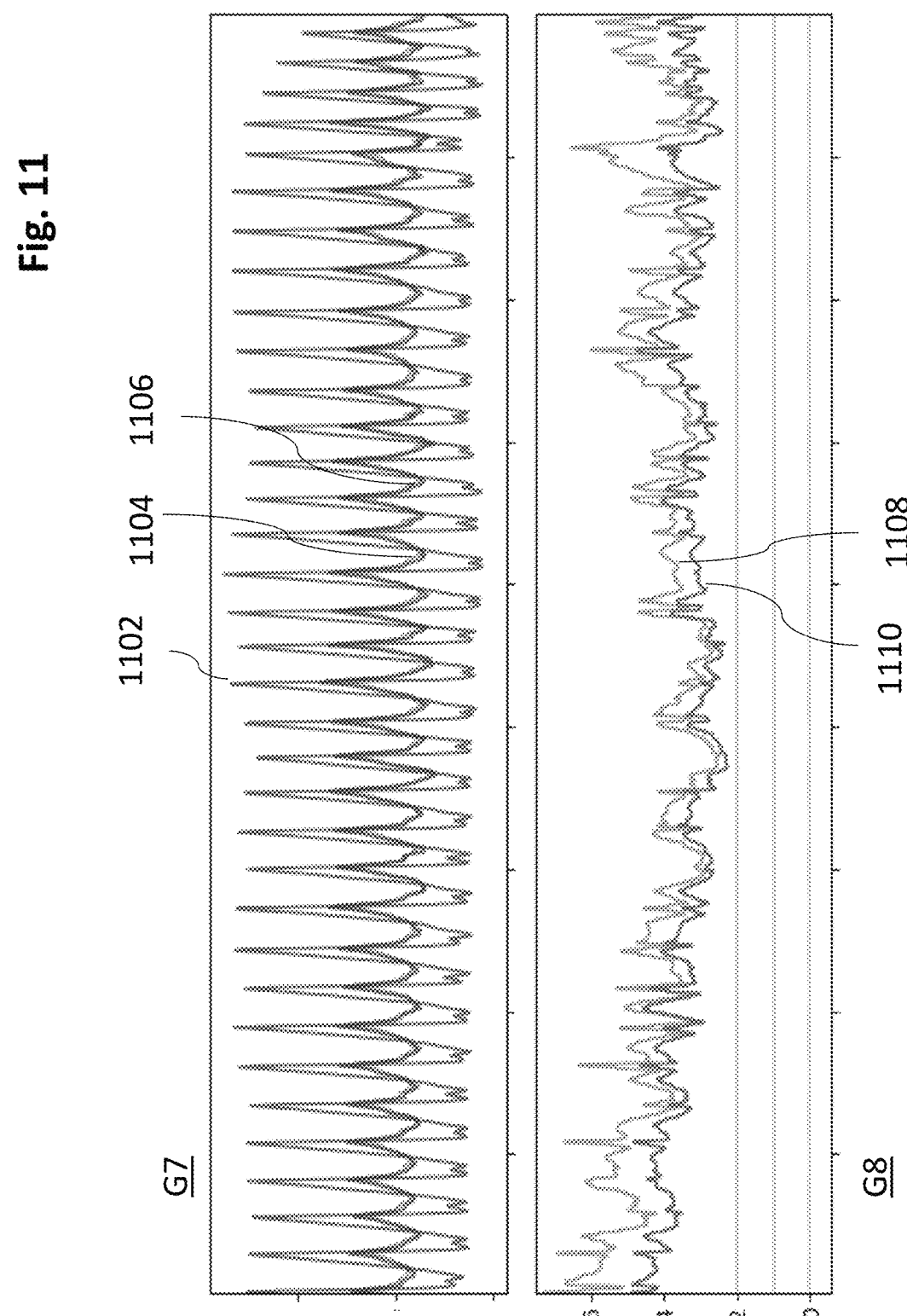
Figure 12:
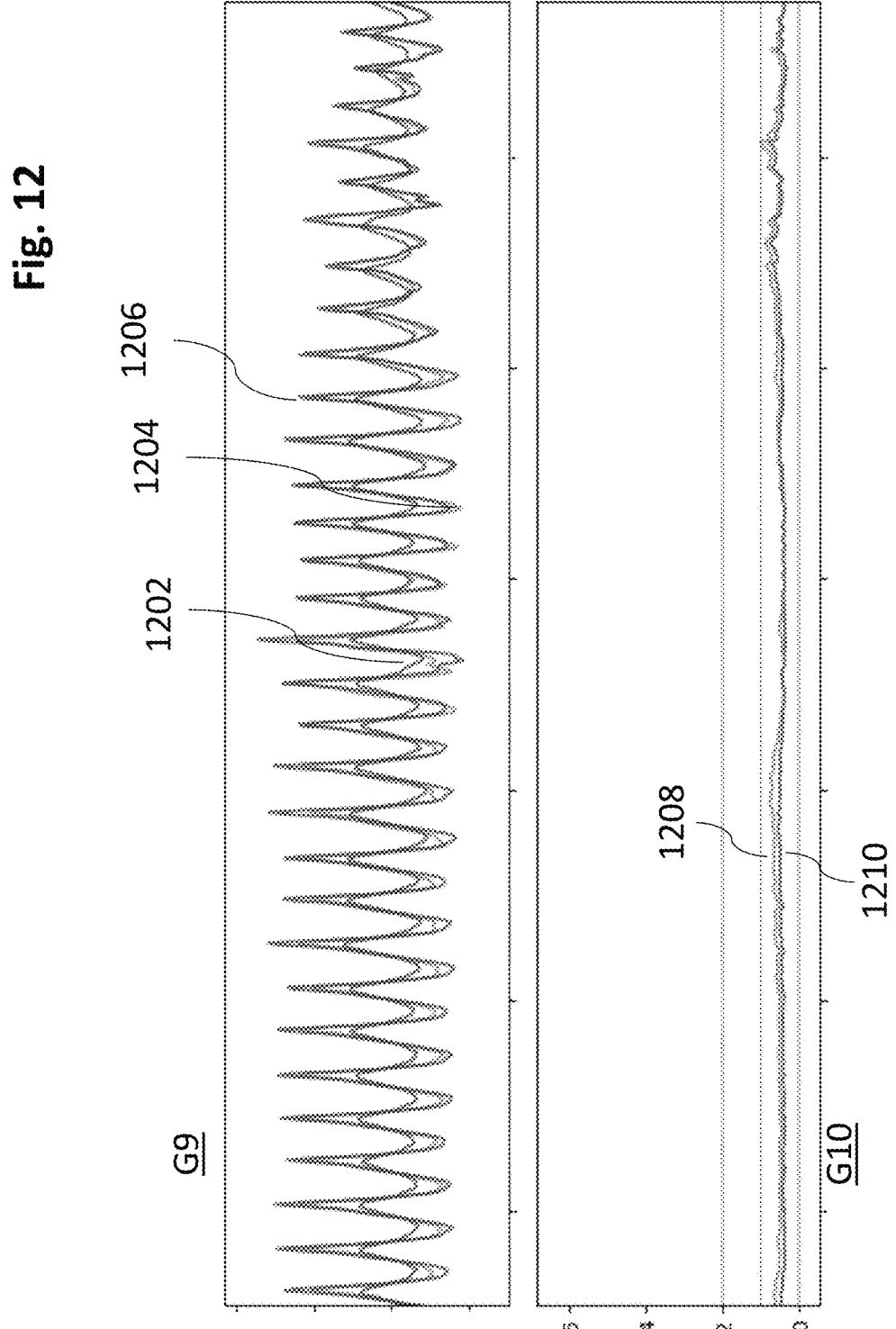
Figure 13:
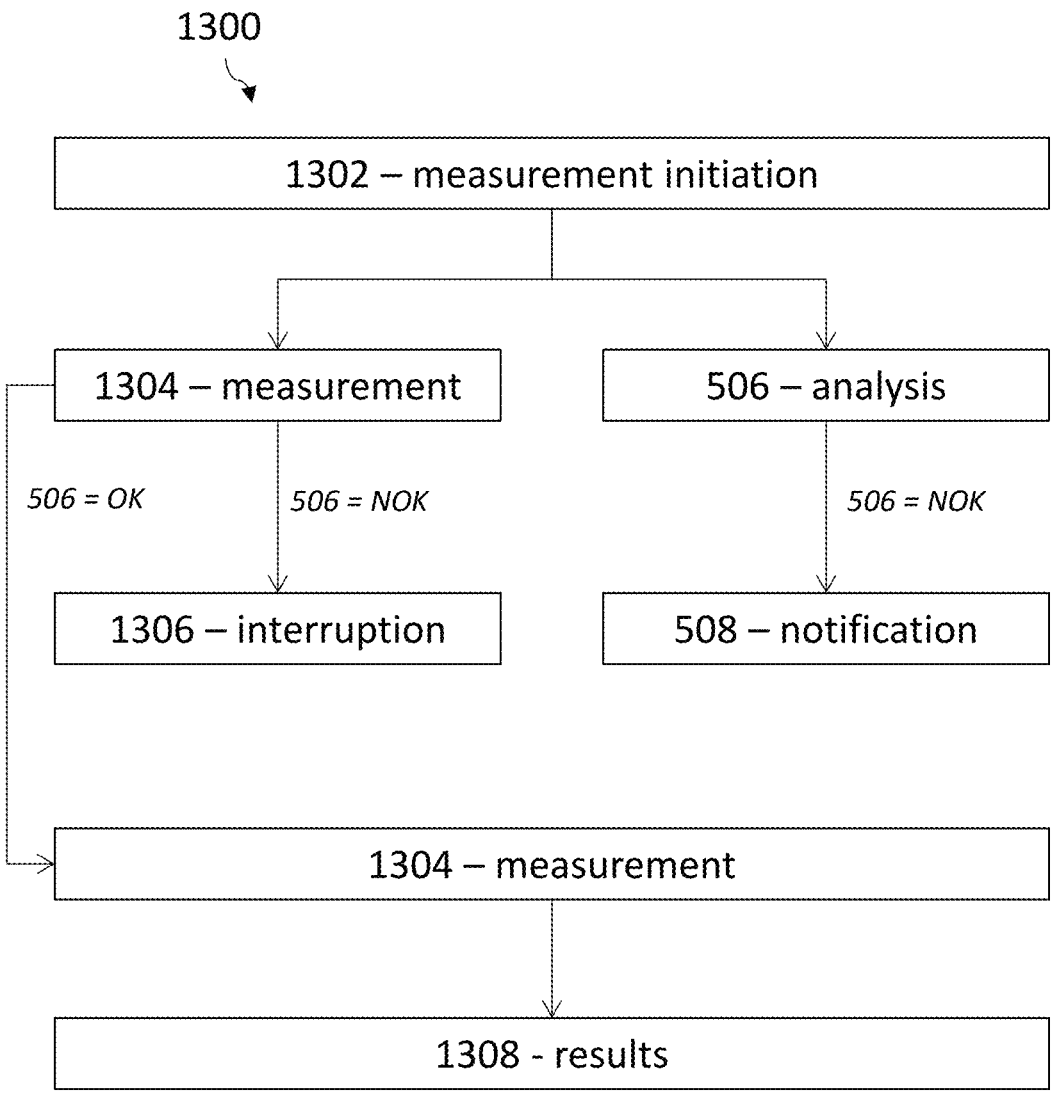

For a better understanding of the embodiments described, reference is made to the figures shown below:

FIG. 1 shows a front side of an example of a measuring device conforming to an embodiment of the invention, FIG. 2 shows a rear side of the example measuring device of FIG. 1, FIG. 3 shows a diagram of the components and/or functions of a measuring device conforming to an embodiment of the invention, and of an example of a computer system integrating such a measuring device, FIG. 4 shows an example of an absorption curve as a function of wavelength, and an example of a tissue penetration depth diagram as a function of wavelength, FIG. 5 shows a diagram of an evaluation method according to one aspect of the present description, FIG. 6 shows a detailed diagram of a step in the evaluation method according to one aspect of the present description, FIG. 7 shows a curve illustrating a PPG signal with the continuous component and the pulsatile component of the PPG signal, FIG. 8 shows a curve representing a PPG signal normalized by the DC component and a perfusion index, for three different wavelengths, when a contact pressure between the optical sensor and the skin is considered correct, FIG. 9 shows a curve representing a PPG signal normalized by the DC component and a perfusion index, for three different wavelengths, when a contact pressure between the optical sensor and the skin is considered too high, FIG. 10 shows a detailed diagram of a step in the evaluation method according to one aspect of the description, FIG. 11 shows a curve representing a PPG signal normalized by the DC component and a vascular parameter, according to an embodiment of the invention, when a contact pressure between the optical sensor and the skin is considered correct, FIG. 12 shows a curve representing a PPG signal normalized by the DC component and a vascular parameter, according to an embodiment of the invention, when a contact pressure between the optical sensor and the skin is considered too high, FIG. 13 shows a diagram of a physiological measurement method.

DETAILED DESCRIPTION

The following description presents various examples of measuring devices and associated methods that use a PPG-type optical signal to determine a contact pressure level between the measuring device and a user's skin.

A measuring device according to the present description is capable of obtaining optical signals and detecting a contact pressure level between the user and the measuring device. The measuring device may comprise a housing, an optical sensor configured to detect an optical signal (in particular a PPG sensor configured to detect a PPG signal), and a processor housed in the housing configured to implement a method of processing the detected optical signal. The evaluation method according to the present description may identify excessive pressure between the optical sensor and the skin, which results in the optical signal not being of sufficient quality to obtain a physiological measurement (e.g. heart rate HR, blood oxygen saturation rate SpO2, blood pressure or glucometry, etc.). Measuring devices may also include a user interface capable of conveying a message to the user. The interface may take different forms: screen, pointer, vibrator, loudspeaker, etc., and the message may be of different kinds, depending on the interface: visual message, audio message, haptic message, etc.

The optical sensor (e.g. a PPG sensor) comprises, in a simplified form, at least one light source (e.g. a light-emitting diode, or LED), suitable for emitting light towards the user's skin, and at least one light receiver (e.g. a photoreceptor), suitable for receiving light that passes through, reflects, scatters or diffracts in the user's biological tissues. The optical signal depends on the tissue traversed. In particular, a PPG signal comprises light that has been optically modulated by volumetric variations in arteries, arterioles or capillaries.

The light source(s) may emit light at one or more wavelengths that are chosen according to the type of physiological measurements the measuring device may perform. The wavelengths used on PPG measuring devices include green (or yellow), red and infrared. The light receiver(s) may receive light at the corresponding wavelength(s). In particular, the measuring device comprises an optical sensor capable of operating at at least two wavelengths.

The optical sensor may be positioned at any suitable location on the measuring device, and in particular on any side of the case. When the measuring device is a watch, the optical sensor is placed on the back of the watch, to be in contact with the skin during normal use.

The optical signal measured by the optical sensor may depend on the nature of the contact between the optical sensor and the skin, and in particular on the contact pressure with which the optical sensor presses on the skin (or conversely, the force with which the user presses on the optical sensor). In fact, a measuring device with low contact pressure may result in weak optical contact, reducing the amount of light penetrating the skin and consequently lowering the quality of the optical signal obtained by the optical sensor. Conversely, too high a contact pressure may force blood out of certain superficial vessels, altering the shape and amplitude of the optical signal in relation to the application pressure at which a physiological measurement (HR, SpO2, etc.) and its algorithm have been calibrated.

With reference to FIG. 1 and FIG. 2, an example of a measuring device 100 in the form of a connected watch is shown. The measuring device 100 may comprise a housing 102 and a user interface 104. The function of the user interface 104 is to communicate information to a user. The user interface 104 may comprise hands 106 (for example, the hands that indicate the time or an additional hand that may indicate other information such as the number of steps) and/or a display 108 (OLED, PMOLED, etc.). The display 108 may or may not be touch-sensitive. The user interface 104 may comprise, alternatively or complementarily, one or more components not visible in FIG. 1, such as a vibrator or speaker. Hands 106 and screen 108 enable visual information to be transmitted (visual user interface), while the loudspeaker enables sound information to be transmitted and the vibrator enables haptic information to be transmitted (haptic user interface). Other user interface means may be used to transmit information to the user.

The measuring device 100 may also include an interaction mechanism 110 between the user and the watch. In the example shown, the interaction mechanism 110 may comprise a rotatable and pressable crown, but any type of button may be envisaged. The interaction mechanism 110 may comprise a touch screen, for example screen 108, instead of or in addition to a crown.

To attach the measuring device 100 to the wrist, fastening or tightening means 112 may be provided, attached to the housing 102, for example in the form of a bracelet.

FIG. 2 illustrates a rear side 200 of the measuring device 100, intended to be on the user's skin. On this rear side 200, the measuring device 100 comprises an optical sensor 202, for example a PPG sensor. The optical sensor 202 comprises one or more light sources 204 and one or more light receivers 206. In the illustrated example, the measuring device 100 comprises three light sources (in the example, LEDs), shown at 204, emitting wavelengths in the green, red and infrared, and comprises two light receivers 206, 208 (in the example, photodiodes)-one for green and the other for red and infrared. Any configuration capable of generating optical signals in two wavelengths is suitable. In particular, the optical sensor may be arranged differently (light source and receivers not aligned with each other, etc.).

When the measuring device 100 is worn on the wrist, the rear face 200 is generally in contact with the skin, which means that the optical sensor 100 is positioned to be able to emit and receive light towards the skin, as described previously. The contact pressure depends in particular on how tightly the tightening means 112 is tightened on the user's wrist.

Alternatively (not shown), the optical sensor could be arranged elsewhere on the measuring device housing, and the user could simply place his finger on the optical sensor.

FIG. 3 shows a diagram 300 of the components that may be included in the measuring device 100, and the overall system into which the measuring device 100 fits. The measuring device 100 comprises a control circuitry 302 with a processor 304, a memory 306 and an I/O interface 308 (input/output) configured to send and receive data to/from control circuitry 302. A communication module 310 may be provided for exchanging data with an external terminal (e.g. a smartphone). The communication module 310 may be a wireless module, such as Wi-Fi, Bluetooth, Bluetooth Low Emission, etc. In particular, control circuitry 302 may exchange with the optical sensor 202, to obtain optical signals to determine whether the contact pressure between the optical sensor 202 and a user's skin is acceptable or not, and may activate the user interface 104 to notify the user to modify the relative positioning between the skin and the optical sensor 202.

In addition to the optical sensor 202, the measuring device 100 may include various sensors 312: accelerometer, GPS sensor, compass, temperature sensor, ECG (electrocardiogram), BIA (bioimpedance analysis) etc., which are connected to the I/O interface 308. Electrical or electronic links between the various components are provided by one or more buses 314.

The measuring device 100 may include a battery 316 to supply power to the components.

Memory 306 may store instructions which, when executed by processor 304, implement the method(s) of the present description. Preferably, the methods are fully implemented by the measuring device 100, in particular by the processor 304 of the measuring device 100 (so-called "local" execution). This means that the result of implementing these methods is available to the user without requiring an external connection, in particular with an external terminal (such as a smartphone).

The measuring device 100 may communicate, using the communication module 310 and a communication network 318, with an external terminal 320, such as an intelligent mobile terminal (smartphone). The external terminal 320 comprises control circuitry 322 with a processor 324, a memory 326 and an I/O interface 328 configured to send and receive data from control circuitry 302. The external terminal 320 further comprises a user interface 330 for interacting with the user. The processor 324 and memory 326 may implement an application that enables the external terminal 320 to communicate with the measuring device 100. In particular, the user interface 330 may display information for the user.

The measuring device 100 may also communicate with a server 332, either directly via the communication network 318 or via the external terminal 320. The server 332 may store the measurements made by the watch (cloud architecture).

The communication network may be heterogeneous: short-range wireless (Bluetooth, Wi-Fi, etc.), long-range wireless (cellular, etc.), wired (Ethernet, etc.).

In an embodiment, the measuring device 100 is a wearable device, i.e. a device designed to be worn on the human body. In the example shown in FIG. 1 and FIG. 2, the wearable device 100 is a watch and the user's skin is the skin of the wrist. In other examples, the measuring device 100 may be a measuring handle fitted to a scale, an earbud or earpiece, a finger clip or a housing for other purposes, a patch, etc. However, the problem of over-tightening generally concerns devices where the user has a direct influence on the contact pressure, for example by adjusting the tightening means.

FIG. 4 illustrates two graphs G1 and G2 showing the biophysical principles involved in the methods and devices described herein. Graph G1 represents, in a logarithmic scale, the molar extinction coefficient of hemoglobin and oxyhemoglobin as a function of wavelength λ. To first order, this coefficient may be likened to absorption: it shows that green light (e.g. wavelengths below 600 nm) is much more strongly absorbed than red and infrared light (e.g. wavelengths above 650 nm). Graph G2, from the publication "Development of a Portable All-Wavelength PPG Sensing Device for Robust Adaptive-Depth Measurement: A Spectrometer Approach with a Hydrostatic Measurement Example", Chang et al. in Sensors (DOI: 10.3390/s20226556), illustrates the penetration depth into the skin (ordinate) of different wavelengths Å (abscissa). Typically, green penetrates to around 0.3 mm, while red and infrared penetrate to 3 mm.

FIG. 5 illustrates the steps of an evaluation method 500 according to an embodiment of the invention. This method is based on the use of one or more light sources emitting at two distinct wavelengths. These different wavelengths penetrate the user's body at different depths and generate optical signals with different properties depending on the presence or absence of blood at different depths. Evaluation method 500 may be implemented in conjunction with a physiological measurement method: HR, SpO2, blood pressure, glucometry, etc.

In a determination step 502, control circuitry 302 determines first optical data from a first optical signal obtained by optical sensor 202 working at a first wavelength λ1. In a determination step 504, control circuitry 302 determines second optical data from a second optical signal obtained by the from the optical sensor 202 working at a second wavelength λ2. The second wavelength λ2 is different from the first wavelength λ1.

In an embodiment, the first wavelength λ1 is less than 600 nm, or even less than 540 nm, and the second wavelength λ2 is strictly greater than 600 nm, or even greater than 650 nm.

In an embodiment, the first wavelength λ12 is between 500 nm and 600 nm and the second wavelength λ2 is between 600 nm and 1000 nm.

In an embodiment, the first wavelength λ1 is between 440 nm and 540 nm and the second wavelength λ2 is between 650 nm and 665 nm.

Furthermore, the difference between the second wavelength λ2 and the first wavelength λ1 may be at least 50 nm, in order to benefit more from the effect related to the difference in penetration depth between the wavelengths, as illustrated in graph G2 of FIG. 4, and/or to benefit more from the effect related to absorption by hemoglobin, as illustrated in graph G1 of FIG. 4.

In an embodiment, the first wavelength λ1 is in the green (or blue or yellow) and the second wavelength λ2 is in the red or infrared (near infrared in particular).

In an embodiment, the optical signals are PPG signals, i.e. optical signals representative of volume variations. In an embodiment, the signals are representative of variations in velocity. More generally, the optical signals are signals that measure physical characteristics that vary with heart rate.

Determination steps 502 and 504 may be carried out simultaneously, consecutively or overlapping. When they are performed consecutively, step 502 may be performed before or after step 504.

In an analysis step 506, control circuitry 302 analyzes the optical data generated by the determination steps 502, 504. The analysis may comprise a combination of the first optical data and the second optical data in order to compare them with each other. In an embodiment, the analysis generates information relating to the contact pressure between the optical sensor and the skin, by means of the comparison between the first optical data and the second optical data. In particular, the analysis may comprise a comparison of the first optical data and the second optical data. The comparison may be made by calculating a parameter that depends in particular on the presence of blood in the superficial tissues (hereinafter referred to as the vascular parameter), i.e. the value of the parameter enables the first optical data and the second optical data to be compared with each other. For example, the comparison of the first optical data and the second optical data may be carried out using a ratio or a subtraction, i.e. the calculation of the parameter comprises the calculation of a ratio or a subtraction respectively. In particular, analysis step 506 may be used to determine whether a contact pressure between the skin and the pressure sensor is too high, in particular to obtain a physiological quality measurement. In practice, the optical data may be used to determine information relating to the presence of blood in the skin's superficial tissues. The vascular parameter may therefore be used to deduce information about the contact pressure between the sensor and the skin. Analysis 506 may involve comparing the value of the vascular parameter with a threshold. In an embodiment, the threshold may be predetermined, so that analysis step 506 does not require calibration on the user.

In a step 508, control circuitry 302 may generate, for the user interface 104, notification instructions for the user based on the result of the analysis in step 506. The notification may include an indication relating to the contact pressure between the skin and the optical sensor 202, i.e. more generally between the skin and the measuring device 100. The indication may warn the user that the optical sensor 202 is pressing too hard on the skin. For example, the measuring device 100 may vibrate and/or display a message indicating that a wristband should be loosened.

Optical data acquisition steps 502, 504 and analysis step 506 will be described in greater detail.

Determination of Optical Data

FIG. 6 shows a diagram 600 illustrating the details of determination steps 502, 504, according to an embodiment. In an emitting step 602, control circuitry 302 instructs the light source 204 of the optical sensor 202 to emit an optical signal at a given wavelength (λ1, λ2, etc.). In a reception step 604, which is concomitant with step 602 due to the speed at which the light travels, control circuitry 302 instructs the light receiver(s) 206, 208 of the optical sensor 202 to receive the optical signal that has passed through the user's biological tissues (e.g. at wrist level). With identical light source and light receiver positioning, the path taken by the light in the user's body depends on the wavelength of the optical signal, as explained in relation to graph G2 in FIG. 4. Finally, in a processing step 606, control circuitry 302 processes the received optical signal to generate the optical data associated with the optical signal. Different types of processing may be applied. In particular, processing may involve extracting pulsatile data from the received optical signal. Transmitting step 602, receiving step 604 and processing step 606 are implemented for each wavelength used in the evaluation method 500. As previously indicated, the received optical signal may be a PPG signal.

FIG. 7 shows a graphical representation 700 of an optical signal 702 received by the optical sensor 202, with time t on the abscissa and absorption A (in arbitrary units) on the ordinate; this is a PPG signal. This optical signal 702 may be broken down into several components: a so-called continuous component (called DC), which varies little as a function of the heartbeat, and a so-called pulsatile component (called AC), which varies more strongly as a function of the heartbeat. The DC component corresponds to the amplitude of the received optical signal as modulated by the tissues (region 704), by venous blood (region 706), which is not subject to pulsatility in the bloodstream, and by non-pulsatile arterial blood (region 708), i.e. the quantity of blood permanently present in the arteries. The AC component corresponds to the modulation by pulsatile arterial blood of the amplitude of the optical signal received (region 710). The time between two peaks of optical signal 702 corresponds to one cardiac cycle.

The optical signal received, and in particular the DC component of this signal, depends in particular on the intensity and wavelength of the emitted optical signal. For example, if the emitted light intensity is increased, then the DC component will be larger. In another example, depending on the wavelength and equal intensity of the emitted optical signal, the amplitude of the received optical signal, and in particular the amplitude of the pulsed AC component, is not equal, due to differences in absorbance values. Consequently, normalization of the PPG signal or of the pulsatile AC component of the PPG signal by the DC component is generally implemented to overcome these variabilities as far as possible.

The article "Signal processing and calibration improve blood measurements" by Marc Smith on edn.com (https://www.edn.com/signal-processing-and-calibration-improve-blood-measurements/) provides further explanation of PPG.

Processing Step 606

The processing step 606, which generates the optical data Opt, may be performed in various ways. In an embodiment, control circuitry 302 calculates a perfusion index (called I) which corresponds to the ratio of the pulsatile AC component of the received optical signal to the DC component of the received optical signal. $Opt=I=AC/DC$. The perfusion index may also be simply called perfusion or normalized pulsatile amplitude (due to division by the DC component). The pulsatile and continuous components vary with time, so that $I(t)=AC(t)/DC(t)$. A perfusion index I is calculated for a given wavelength, so that I may be written, $I_\lambda$.

Accordingly, acquisition steps 502 and 504, during which control circuitry 302 determines optical data, may include processing the received optical signals to calculate a perfusion index I for each wavelength. The first optical data Opt1 is therefore the perfusion index IM of the optical signal received at the first wavelength $\lambda 1$ ($Opt1=AC_{\lambda 1}/DC_{\lambda 1}$) and the second optical data Opt2 is the perfusion index $I_{\lambda 2}$ of the optical signal received at the second wavelength $\lambda 2$ ($Opt1=AC_{\lambda 2}/DC_{\lambda 2}$).

The use of the perfusion index as optical data for the methods and devices described herein is of multiple interest. Firstly, it is a datum that is used in particular for determining the SpO2 oxygen saturation rate (see EP3903677, for example). Consequently, calculating it using the optical sensors and methods present in smartwatches available at the date of filing of the present description does not pose any difficulty or generate any technical burden. Secondly, this data highlights the pulsatility of blood circulation; in the absence of blood, pulsatility is greatly reduced, which is visible in the data.

Document EP3903677 describes various techniques for calculating AC and DC components (using filters and/or subtractors in particular).

FIG. 8 illustrates a plurality of curves in the case of a measuring device 100 with a contact pressure considered appropriate between the optical sensor 202 and the skin: graph G3 illustrates the PPG signals (i.e. the received and filtered optical signal) normalized by the DC component of each PPG signal for wavelengths in green (curve 802), red (curve 804) and infrared (curve 806) and graph G4 illustrates the perfusion index I for wavelengths green (curve 808), red (curve 810) and infrared (curve 812). In other words, graph G4 illustrates the evolution of the amplitude of the curves in graph G3. Note that the perfusion index of the green optical signal is much higher than the perfusion index of the red and infrared optical signals, which is low (between 0 and 1). The units of graph G3 are arbitrary.

FIG. 9 illustrates a plurality of curves in the case of a measuring device 100 with excessive contact pressure between the optical sensor 202 and the skin: graph G5 illustrates the PPG signals (i.e. the received and filtered optical signal) normalized by the DC component of each PPG signal for green (curve 902), red (curve 904) and infrared (curve 906) wavelengths, and graph G6 illustrates the perfusion index I for green (curve 908), red (curve 910) and infrared (curve 912) wavelengths. In other words, graph G6 illustrates the evolution of the amplitude of the curves in graph G5. It shows that the perfusion index of the green optical signal is lower than the perfusion index of the red and infrared optical signals. The units of graph G5 are arbitrary.

FIG. 8 and FIG. 9 illustrate the first optical data when the first wavelength $\lambda 1$ corresponds to green, and the second optical data when the second wavelength $\lambda 2$ corresponds to red or infrared.

In an embodiment, processing step 606 may comprise a subsequent step of extracting the extrema of the perfusion indexes I and/or calculating a time average of the perfusion indexes I, so that the optical data are the extrema or averages of the perfusion indexes. The time average may be calculated as an average over a sliding window of a few seconds (e.g. from one to three seconds). In an embodiment, processing step 606 may comprise calculating a time average of the absolute value of perfusion index I. This subsequent step avoids having to work with the entire perfusion index, and therefore saves resources (processor, memory, battery, which must be optimized). The term perfusion index I will also be used to cover the data as processed by the subsequent step.

Other signal processing methods for extracting pulsatility from the optical signal may be suitable.

Alternatively, the optical data may be generated in ways different from those described above. For example, processing step 606 may simply involve extracting the pulsatile AC component. If the optical signals are sufficiently different between two wavelengths, the pulsatile AC component may suffice to discriminate them: in this case, $Opt1=AC_{\lambda 1}$ and $Opt2=AC_{\lambda2}$ may be used. Similarly, the DC component alone may suffice, since the DC component tends to decrease as blood is expelled from superficial tissues: in this case, $Opt1=DC_{\lambda1}$ and $Opt2=DC_{\lambda2}$ may be used. Other, less common, quantities may be used, such as AC(t)/DC(t0), where to is a given time and AC(t) is the pulsatile component that varies with time, or AC(t)/avg(DC(t)), where avg(DC(t)) is the average of the DC component over a given time interval. PPG(t)/DC(t) may also be used. In the same way as described above, a subsequent extrema extraction or time-averaging step may be performed to generate the optical data.

Description of Optical Data Analysis

FIG. 10 shows a diagram 1000 illustrating the details of analysis step 506 in an embodiment.

In a calculation step 1002, control circuitry 302 performs the comparison by calculating a vascular parameter P. The vascular parameter P is data obtained using and from a combination of the first optical data and the second optical data, enabling them to be compared with each other. Formulated differently, if we call the first optical data Opt1 and the second optical data Opt2, we define the function F for calculating the parameter P as follows: F:(Opt1, Opt2)=>F (Opt1, Opt2)=P, whose value is a real number. The function F is a function chosen to compare the first optical data with the second optical data (and vice versa). In particular, the function F may comprise a ratio, such that the vascular parameter is between the first optical data and the second optical data, such that P=F(Opt1, Opt2)=Opt1/Opt2 or P=F (Opt1, Opt2)=Opt2/Opt1 (referred to as a "ratio of ratios"). In an embodiment, the vascular parameter is formed solely by the ratio (without the addition of other data). The advantage of a ratio is that it allows the measuring device to operate in relative terms, and therefore to have a vascular parameter that is independent of the external factors already mentioned. Nevertheless, the function F may include subtraction, with normalization (e.g. (Opt1-Opt2)/Op2) or without normalization (e.g. (Opt1-Opt2)). Other treatments may be applied (absolute value, squaring, etc.).

FIG. 11 illustrates a plurality of curves in the case of a measuring device 100 with a contact pressure considered appropriate between the optical sensor 202 and the skin: graph G7 (similar to graph G3) illustrates PPG signals (i.e. optical signals received and filtered) normalized by the DC component of each PPG signal for wavelengths in the green (curve 1102), red (curve 1104) and infrared (curve 1106) and graph G8 illustrates the vascular parameter as the ratio of ratios (P=Opt1(green)/Opt2(red or infrared)) for the wavelengths green/red (curve 1108), and green/infrared (curve 1110). The units in graph G7 are arbitrary. Note that the vascular parameters green/red and green/infrared are well above1.

FIG. 12 illustrates a plurality of curves in the case of a measuring device 100 with excessive contact pressure between the optical sensor 202 and the skin: graph G9 (similar to graph G5) illustrates PPG signals (i.e. optical signals received and filtered) normalized by the DC component of each PPG signal for wavelengths in the green (curve 1202), red (curve 1204) and infrared (curve 1206) and graph G10 illustrates the vascular parameter as the ratio of ratios (P=Opt1(green)/Opt2(red or infrared)) for the wavelengths green/red (curve 1208), and green/infrared (curve 1210). The units in graph G9 are arbitrary. Note that the vascular parameters green/red and green/infrared are almost always less than 1.

In a comparison step 1004, control circuitry 302 may perform a comparison of the vascular parameter value against a threshold. As already explained, it is expected that the optical data associated with the wavelength that penetrates the least into the tissues will be altered when pressure is applied to the skin at the location of the optical sensor 202: this modification is therefore reflected in the value of the vascular parameter. By comparing the value of the vascular parameter with a threshold, it is possible to assess the pressure applied to the skin. In particular, it has been explained that the pulsatile AC component of the PPG optical signal at the first wavelength $\lambda1$ is strongly attenuated when the contact pressure is too great.

If the comparison indicates that the value of the vascular parameter P is greater (in the case where the parameter varies in the same direction as the contact pressure, or respectively less if it varies in the opposite direction to that of the contact pressure) than a threshold, control circuitry 302 may implement the step 508 of generating instructions for notification; if the comparison indicates that the value of the vascular parameter is less (or respectively greater) than the threshold, control circuitry 302 may terminate 1006 the execution of the method. Whether the vascular parameter will vary in the same or opposite direction to that of the contact pressure depends on the definition of the blood parameter. Other conditions may be invoked to implement step 508, for example conditions linked to the calculation of a second vascular parameter with a third wavelength (see below).

The comparison in step 1004 may be carried out in various ways: control circuitry 302 may simply compare the value of the vascular parameter at each point in time or at regular time intervals, to check whether at least one value is above or below the threshold; control circuitry 302 may compare using an aggregation method (to take account of the proportion of the time the vascular parameter is below or above the threshold); control circuitry 302 may compare an average of the vascular parameter (for example, an average over a sliding window), and so on.

The threshold may be predetermined, so that it does not depend on the user (but only on the measuring device 100 and in particular on the technical specifications of the optical sensor 202), thus avoiding the need to calibrate the measuring device for each user.

In the case of the embodiment where the optical data are a perfusion index as illustrated in FIG. 8 and FIG. 9, the vascular parameter P may be a ratio between perfusion indexes:control circuitry 302 may then compare the ratio $I_{\lambda1}$ to $I_{\lambda2}$ with respect to a threshold K. As previously explained and illustrated in FIG. 8 and FIG. 9, the perfusion index at the first wavelength $\lambda1$ (corresponding to green, for example) drops significantly if contact pressure is too high, whereas the perfusion index at the second wavelength $\lambda2$ (corresponding to red or infrared, for example) is little affected whatever the contact pressure. Comparing the ratio of perfusion indexes with a threshold makes it possible to evaluate variations in the perfusion index at the first wavelength $\lambda1$ free from changes in conditions with normalization by the perfusion index at the second wavelength $\lambda2$. Indeed, the perfusion index may vary according to various factors: temperature, optical sensor location on the skin, blood pressure, peripheral blood circulation variation, skin color, hairiness, etc. Normalization reduces the influence of these factors and enables indexes to be compared with a predetermined threshold. By predetermined, we mean a threshold which does not depend on the user (and which can, in the event of modification, be updated via the communication network 318). This allows the method to be used widely and immediately, without calibration by the user and therefore without any action on his part.

Typically, if control circuitry 302 determines that $P=I_{\lambda 1}/I_{\lambda 2}=(AC_{\lambda 1}/DC_{\lambda 2}/(AC_{\lambda 2})>K$, then the contact pressure is deemed acceptable (end step 1006); but if control circuitry 302 determines that $P=I_{\lambda 1}/I_{\lambda 2}\leq K$, then the contact pressure is deemed too high and in this case, control circuitry 302 may continue with notification step 508.

The threshold K depends on the configuration of the optical sensor 202 and the methods used to determine the optical data. However, depending on the nature of the green, red and/or infrared perfusion index, the threshold K may be chosen between 0.5 and 5 or between 0.5 and 2. In an embodiment, the threshold K is set to 1. This means that the analysis step 506 and in particular the comparison step 1004 directly compares the perfusion index $I_{\lambda 1}$ of the first wavelength $\lambda 1$ with the perfusion index $I_{\lambda 2}$ of the second wavelength $\lambda 2$. When the contact pressure is acceptable, blood is present in the superficial tissues in normal quantities and the perfusion index $I_{\circ 1}$ of the first wavelength $\lambda_1$ is greater than the perfusion index $I_{\lambda 2}$ of the second wavelength $\lambda 2$. When the contact pressure is too high, blood is less present in superficial tissues and the value of the perfusion index $I_{\lambda 1}$ of the first wavelength $\lambda 1$ becomes lower than the value of the perfusion index $I_{\lambda 2}$ of the second wavelength $\lambda 2$.

In the example in FIG. 11, the value of the vascular parameter (calculated for green/IR, green/red pairs) is always greater than the threshold set at 1. In the example in FIG. 12, the value of the vascular parameter (calculated for green/IR, green/red pairs) is always less than the threshold set at 1.

In an embodiment, several thresholds may be provided, in order to refine the contact pressure assessment. For example, the value of the vascular parameter may be compared with a first threshold K and a second threshold K', with K'<K. Depending on the value of the vascular parameter, in particular by means of these comparisons with the first threshold K and the second threshold K', it is possible to order the contact pressures and, for example, adapt the instructions to the user. For example, the instructions may include slightly loosening the measuring device (if the parameter is between K' and K) or firmly loosening the measuring device (if the parameter is below K').

Notification

The notification to the user may be a visual message whose content tells the user to reduce the contact pressure between the optical sensor 202 and the skin. For example, the notification may indicate: "loosen the wristband", "release the pressure a little", "press a little less hard", or it may be a drawing. Alternatively or complementarily, the notification may include a vibration, a light or a sound.

Three Wavelengths Embodiment

In an embodiment, three wavelengths are used to implement the methods described. Therefore, what has been described for two wavelengths applies similarly to three wavelengths $\lambda 1, \lambda 2, \lambda 3$. In particular, the first wavelength $\lambda 1$ may be less than 600 nm, the second wavelength $\lambda 2$ may be between 600 nm (strictly above 600 nm) and 800 nm (e.g. 655 nm), and the third wavelength $\lambda 3$ may be between 800 and 1000 nm. As before, it is preferable to have at least 50 nm between the first wavelength $\lambda 1$ and the second wavelength $\lambda 2$.

In an embodiment, the wavelengths are chosen as follows: 480 nm<$\lambda 1$<540 nm; 650 nm<$\lambda 2$<665 nm; 920 nm<$\lambda 3$<960 nm.

Analysis step 506 then comprises a double comparison between, on the one hand, the first optical data relating to the first wavelength $\lambda 1$ and the second optical data relating to the second wavelength $\lambda 2$, and, on the other hand, the first optical data relating to the first wavelength $\lambda 1$ and the third optical data relating to the third wavelength $\lambda 3$. Control circuitry 302 then calculates two vascular parameters (the first vascular parameter P12 from the first optical data and the second optical data, the second vascular parameter P13 from the first optical data and the third optical data).

In the case of optical data in the form of a perfusion index ratio I, step 506 may include a double comparison: if $P12=I_{\lambda 1}/I_{\lambda 2}<K12$ and if $P13=I_{\lambda 1}/I_{\lambda 3}<K13$ (where K12 and K13 are two thresholds, for example predetermined and not dependent on the user) then the contact pressure is deemed too high and control circuitry 302 may continue with notification step 508. In an embodiment, K12=K13=K. The choice of imposing that, in step 506, each comparison must be checked to assess the contact pressure as too high makes the assessment method more robust. Alternatively, the contact pressure may be evaluated as too high if at least one of the comparisons is verified, if a more permissive evaluation method is desired (which amounts to replacing the "and" with an "or" in the formula given above).

In an embodiment, the vascular parameter is stored in the memory for later use, for example to evaluate the quality of a measurement. In this case, the measuring device may not send a notification to the user, so that the evaluation method 500 does not include any interaction with the user (no notification step 508).

Application to a Measurement Method

The evaluation method 500 as described above may be integrated into a physiological measurement method 1300, represented by the diagram in FIG. 13. In a measurement initiation step 1302, control circuitry 302 may initiate an optical measurement (for example, a SpO2 oxygen saturation level measurement) and start generating optical data. For an SpO2 measurement, the control circuitry 302 calculates the perfusion index(es) for one or more of the wavelengths used (green, red and/or infrared). Consequently, the evaluation method 500 as described here may reuse these perfusion indexes. Thus, acquisition steps 502, 504 are performed, at least partially, by measurement initiation step 1302. While, in a measurement step 1304, control circuitry 302 continues the measurement, control circuitry 302 implements analysis step 506 to determine whether the contact pressure is too high. When analysis step 506 concludes that the contact pressure is too tight (indicated as "506=NOK" in FIG. 13), control circuitry 302 may implement notification instruction generation step 508 at the same time as it interrupts 1306 the measurement. When analysis step 506 concludes that contact pressure is satisfactory (indicated as "506=OK" in FIG. 13), control circuitry 302 lets measurement step 1304 continue. In a results generation step 1308, control circuitry 302 determines a physiological data item from the measurement.

Alternatively, evaluation method 500 may be implemented independently of any physiological measurements.

Design with Different Distances Between Light Source and Receiver

Alternatively or additionally to the user of several different wavelengths, the evaluation method may make use of an optical sensor comprising two light source/light receiver pairs with different distances. In one variant, the optical sensor comprises a light source emitting at a given wavelength and two light receivers arranged so that their respective distance from the light source is different (e.g. in an aligned arrangement). In one variant, the optical sensor comprises two light sources emitting at one wavelength (the respective wavelengths of the two light sources may be the same or different) and one light receiver, arranged so that their respective distance to the light receiver is different (for example in an aligned arrangement). In both variants, the optical path travelled by the light from the light source to the furthest optical sensor is deeper than the optical path travelled by the light from the light source to the nearest optical sensor. This produces first optical data and second optical data, which may be processed by the steps described above. For example, in FIG. 2, light source 204 and light receiver 206 form a first pair used to determine the first optical data; and light source 204 and light receiver 208 form a second pair used to determine the second optical data. In this embodiment, both receivers 206, 208 may be configured to receive light at the same wavelength.

The wavelength used may correspond to one of the wavelengths used previously, so that the values given previously apply similarly.

This embodiment involving different distances between light sources and receivers may be combined with the embodiments involving different wavelengths. In particular, the arrangement of the optical sensor may be such that the closest light source/receiver pair is the one operating at the lowest wavelength.

The present invention may be defined by the following clauses:

1. An evaluation method of a contact pressure between an optical sensor (202) and a user's skin, the method comprising:
   a) determination (502) of first optical data, using a first optical signal obtained by the optical sensor (202) at a first wavelength (λ1), the first optical signal being an optical signal modulated by the heartbeat and the determination (502) comprising processing (606) involving extraction of pulsatile data from the first optical signal,
   b) determination (504) of second optical data, using a second optical signal obtained by the optical sensor at a second wavelength (λ2), different from the first wavelength (λ1), the second optical signal being an optical signal modulated by the heartbeat and the determination (502) comprising processing (606) involving extraction of pulsatile data from the second optical signal,
   c) analysis (506) of at least one comparison of the first optical data with the second optical data, the analysis generating information relating to the contact pressure between the optical sensor and the skin.

2. The evaluation method according to clause 1, comprising:
   d) depending at least on the result of the analysis (506), generation (508) of notification instructions for the user, the notification prompting the user to modify, in particular to reduce, the contact pressure between the skin and the measuring device (100).

3. The evaluation method according to one of clauses 1 to 2, wherein the comparison is carried out by means of the calculation (1004) of a parameter from the first optical data and the second optical data, the parameter making it possible to deduce information relating to the contact pressure between the optical sensor and the skin.

4. The evaluation method according to clause 3, wherein the parameter calculation comprises calculating a ratio between the first optical data and the second optical data.

5. The evaluation method according to one of clauses 3 to 4, wherein the analysis comprises comparison (1004) of the parameter value with a threshold (K).

6. The evaluation method according to clause 5, wherein the threshold (K) is between 0.5 and 10, for example between 0.5 and 2.

7. The evaluation method according to one of clauses 1 to 6, wherein each determination (502, 504) comprises transmitting an optical signal at the given wavelength and receiving the optical signal that has passed through the user biological tissue of the user.

8. The evaluation method according to one of clauses 1 to 7, wherein the first optical data is determined using a first perfusion index and the second optical data is determined using a second perfusion index.

9. The evaluation method according to one of clauses 1 to 8, wherein the first wavelength (λ1) is less than 600 nm and the second wavelength (λ2) is strictly greater than 600 nm, or even greater than 650 nm.

10. The evaluation method according to one of clauses 1 to 9, wherein the first wavelength (λ1) is between 400 and 600 nm and the second wavelength (λ2) is between 600 and 1000 nm.

11. The evaluation method according to one of clauses 1 to 10, wherein the deviation between the first wavelength (λ1) and the second wavelength (λ2) is at least 50 nm.

12. The evaluation method according to one of clauses 1 to 11, wherein the first wavelength (λ1) is less than 540 nm and the second wavelength (λ2) is greater than 650 nm or greater than 800 nm.

13. The evaluation method according to one of clauses 1 to 12, wherein the first wavelength (λ1) is between 480 nm and 540 nm and the second wavelength (λ2) is between 650 nm and 665 nm or between 920 nm and 960 nm.

14. The evaluation method according to one of clauses 1 to 13, wherein the first wavelength corresponds to green, blue or yellow, and the second wavelength corresponds to red or infrared.

15. The evaluation method according to one of clauses 1 to 13, comprising: determination of third optical data, using a third optical signal obtained by the optical sensor at a third wavelength (λ3), different from the first wavelength (λ1) and the second wavelength (λ2), the first optical signal being an optical signal modulated by the heartbeat and the determination (502) comprising a processing (606) involving extraction of pulsatile data from the first optical signal, the analysis (506) comprising analysis of a comparison of the first optical data and the second optical data and analysis of a comparison of the first optical data and the third optical data.

16. The evaluation method according to clause 15, in which the comparisons are carried out by means of a calculation (1004) of a first parameter from the first optical data and the second optical data, and a calculation of a second parameter from the first optical data and the third optical data, the values of the first and second parameters comprising information relating to the contact pressure between the optical sensor and the skin, the analysis (506) comprising the comparison of each of the parameters with a threshold.

17. The evaluation method according to one of clauses 15 to 16, wherein the third length ($\lambda$3) is greater than 800 nm, for example between 800 nm and 1000 nm, for example between 920 nm and 960 nm.

18. The evaluation method according to one of clauses 1 to 17, comprising: initiation (1302) of an optical measurement using the optical sensor and interruption (1306) of the optical measurement depending on the result of the analysis (506).

19. An optical analysis method using an optical sensor (202) configured to contact a user's skin, the method comprising:
   a) determination (502) of first optical data, using a first optical signal obtained by the optical sensor (202) at a first wavelength ($\lambda$1) below 600 nm,
   b) determination (504) of second optical data, using a second optical signal obtained by the optical sensor at a second wavelength ($\lambda$2) greater than 650 nm,
   c) analysis (506) of a comparison of the first optical data and the second optical data.

20. The optical analysis method according to clause 19, comprising:
   d) depending on at least one result of the analysis (506), generation (508) of notification instructions for the user, the notification prompting the user to modify, in particular to reduce, the contact pressure between the skin and the measuring device (100).

21. The optical analysis method according to one of clauses 19 to 20, wherein the analysis (506) comprises calculating (1004) a parameter from the first optical data and the second optical data.

22. The optical analysis method according to clause 21, wherein the parameter calculation comprises calculating a ratio between first optical data and second optical data.

23. The optical analysis method according to one of clauses 21 and 22, wherein the analysis comprises comparing (1004) the parameter value with a threshold (K).

24. The optical analysis method according to clause 23, wherein the threshold is between 0.5 and 10, for example between 0.5 and 2.

25. The optical analysis method according to one of clauses 19 to 24, wherein the optical signals are heartbeat-modulated optical signals, for example photoplethysmography signals.

26. The optical analysis method according to one of clauses 19 to 25, wherein the first optical data are determined using a first perfusion index and the second optical data are determined using a second perfusion index.

27. The optical analysis method according to one of clauses 19 to 26, wherein the first wavelength ($\lambda$1) is between 400 nm and 600 nm and the second wavelength ($\lambda$2) is between 650 nm and 1000 nm.

28. The optical analysis method according to one of clauses 19 to 27, wherein the first wavelength ($\lambda$1) is less than 540 nm and the second wavelength ($\lambda$2) is greater than 650 nm.

29. The optical analysis method according to one of clauses 19 to 28, wherein the first wavelength ($\lambda$1) is between 480 and 540 nm and the second wavelength ($\lambda$2) is between 650 and 665 nm.

30. The optical analysis method according to one of clauses 19 to 29, comprising: initiating (1302) an optical measurement using the optical sensor and interrupting (1306) the optical measurement as a function of the analysis result (506).

31. An evaluation method of a contact pressure between an optical sensor (202) and a user's skin, the method comprising:
   a) determination (502) of first optical data, using a first optical signal obtained by a first light source/receiver pair of the optical sensor (202),
   b) determination (504) of second optical data, using a second optical signal obtained by a second light source/receiver pair of the optical sensor (202), the distance between the light source and receiver of the second pair being greater than the distance between the light source and receiver of the first pair,
   c) analysis (506) of at least one comparison of the first optical data and the second optical data, the analysis generating information relating to the contact pressure between the optical sensor and the skin.

32. The evaluation method according to clause 31, comprising:
   d) depending on at least one result of the analysis (506), generation (508) of notification instructions for the user, the notification prompting the user to modify, in particular to reduce, the contact pressure between the skin and the measuring device (100).

33. The evaluation method according to one of clauses 31 to 32, wherein the analysis (506) comprises calculating (1004) a parameter from the first optical data and the second optical data, the parameter comprising information relating to the contact pressure between the optical sensor and the skin.

34. The evaluation method according to clause 33, wherein the calculation of the parameter comprises the calculation of a ratio between the first optical data and the second optical data.

35. The evaluation method according to one of clauses 33 to 34, wherein the analysis (506) comprises comparing (1004) a parameter value with a threshold (K).

36. The evaluation method according to clause 35, wherein the threshold is between 0.5 and 10, for example between 0.5 and 2.

37. The evaluation method according to one of clauses 31 to 36, wherein the optical signals are heartbeat-modulated optical signals, for example photoplethysmography signals.

38. The evaluation method according to one of clauses 31 to 37, wherein the first optical data and the second optical data are determined using a perfusion index.

39. The evaluation method according to one of clauses 31 to 38, wherein the optical sensor comprises a light source and two light receivers to form the first pair and the second pair.

40. The evaluation method according to one of clauses 31 to 38, wherein the optical sensor comprises two light sources and a light receiver to form the first pair and the second pair.

41. The evaluation method according to one of clauses 31 to 40, comprising: initiation (1302) of an optical measurement using the optical sensor and interruption (1306) of the optical measurement depending on the result of the analysis (506).

42. A computer program product comprising instructions which, when the program is executed by a computer, cause the computer to implement the method according to any of clauses 1 to 18, and/or the method according to any of clauses 19 to 30, and/or according to any of clauses 31 to 41.

43. A measuring device (100) comprising an optical sensor (202) comprising a light source (204) configured to generate light towards a user's skin and a light receiver (206, 208), configured to detect light from the user's skin, wherein the measuring device is configured to implement the method according to one of clauses 1 to 18, and/or the method according to one of clauses 19 to 30, and/or the method according to one of clauses 31 to 41.

44. evice according to clause 43, comprising a wristband (112) for tightening the optical sensor (202) against the user's skin.

45. Use of a comparison of optical data obtained, on the one hand, at a wavelength below 600 nm and, on the other hand, at a wavelength above 650 nm, to assess the presence of blood in superficial tissues.

46. The use according to clause 45, wherein the optical data comprise a perfusion index.

47. The use according to clause 44 or 45, wherein the comparison comprises calculating a ratio.

48. The use according to one of clauses 44 to 46, wherein the result of the comparison is compared with a threshold.

49. The use according to one of clauses 45 to 48, wherein the wavelength below 600 nm corresponds to green and the wavelength above 650 nm corresponds to red or infrared.

The invention claimed is:

1. A notification generation method for evaluating a contact pressure between an optical sensor of a measuring device and a skin of a user, the method comprising:
   a) determining first optical data, using a first optical signal obtained by the optical sensor at a first wavelength, the first optical signal being an optical signal modulated by the heartbeat and the determining of the first optical data comprising processing involving extraction of pulsatile data from the first optical signal, wherein the first optical data comprises the first pulsatile data;
   b) determining second optical data, using a second optical signal obtained by the optical sensor at a second wavelength, different from the first wavelength, the second optical signal being an optical signal modulated by the heartbeat and the determining of the second optical data comprising processing involving extraction of pulsatile data from the second optical signal, wherein the second optical data comprises the second pulsatile data;
   c) analyzing at least one comparison of the first optical data with the second optical data, the analyzing generating information identifying an excessive contact pressure between the optical sensor and the skin, and
   d) depending at least on a result of the analyzing, generating notification instructions for the user, the notification prompting the user to modify the contact pressure between the skin and the measuring device.

2. The notification generation method according to claim 1, wherein the comparison is carried out by calculating a parameter from the first optical data and the second optical data, a value of the parameter being representative of the contact pressure between the optical sensor and the skin, wherein the calculating of the parameter comprises calculating a ratio between the first optical data and the second optical data.

3. The notification generation method according to claim 2, wherein analyzing the at least one comparison comprises comparing a value of the parameter with a threshold.

4. The notification generation method according to claim 3, wherein the threshold is between 0.5 and 10.

5. The notification generation method according to claim 1, wherein each determining of the first and second optical data comprises transmitting an optical signal at, respectively, the first and second wavelengths and receiving, respectively, the first and second optical signals that have passed through the biological tissues of the user.

6. The notification generation method according to claim 1, wherein the first optical data are determined using a first perfusion index and the second optical data are determined using a second perfusion index.

7. The notification generation method according to claim 1, wherein the first wavelength is less than 600 nm and the second wavelength is strictly greater than 600 nm.

8. The notification generation method according to claim 1, wherein the first wavelength is between 400 and 600 nm and the second wavelength is between 600 and 1000 nm.

9. The notification generation method according to claim 1, wherein a difference between the first wavelength and the second wavelength is at least 50 nm.

10. The notification generation method according to claim 1, wherein the first wavelength is less than 540 nm and the second wavelength is greater than 650 nm or greater than 800 nm.

11. The notification generation method according to claim 1, wherein the first wavelength is between 480 nm and 540 nm and the second wavelength is between 650 nm and 665 nm or between 920 nm and 960 nm.

12. The notification generation method according to claim 1, wherein the first wavelength corresponds to green, blue or yellow, and the second wavelength corresponds to red or infrared.

13. The notification generation method according to claim 1, comprising:
   determining third optical data, using a third optical signal obtained by the optical sensor at a third wavelength, different from the first wavelength and the second wavelength,
   the third optical signal being a heartbeat-modulated optical signal and the determining of the third optical data comprising processing involving extraction of pulsatile data from the third optical signal,
   the analyzing comprising analysis of a first comparison of the first optical data with the second optical data and analysis of a second comparison of the first optical data with the third optical data.

14. The notification generation method according to claim 13, wherein the first and second comparisons are carried out by a calculation of a first parameter from the first optical data and the second optical data, and a calculation of a second parameter from the first optical data and the third optical data, wherein values of the first and second parameters comprising information relating to the contact pressure between the optical sensor and the skin, the analyzing comprising a comparison of each of the first and second parameters with a threshold.

15. The notification generation method according to claim 13, wherein the third wavelength is greater than 800 nm.

16. The notification generation method according to claim 1, comprising initiating an optical measurement using the optical sensor and interrupting the optical measurement depending on a result of the analyzing.

17. A non-transitory computer readable medium comprising machine readable instructions which, when the instructions are executed by a computer, cause the computer to implement the method according to claim 1.

18. A measuring device comprising an optical sensor comprising a light source configured to generate light towards a skin of the user and a light receiver, configured to detect light from the skin of the user, wherein the measuring device is configured to implement the method according to claim 1.

19. The measuring device according to claim 18, comprising a wristband for tightening the optical sensor against the skin of the user.

20. The notification generation method according to claim 1, wherein the measuring device is configured to receive a finger on the optical sensor.

21. The notification generation method according to claim 1, wherein determining the first optical data comprises calculating a first perfusion index for the first optical signal and determining the second optical data comprises calculating a second perfusion index for the second optical signal, each perfusion index being a ratio of a pulsatile AC component to a non-pulsatile DC component of the respective optical signal.

22. The notification generation method according to claim 1, wherein analyzing the at least one comparison comprises calculating a parameter as a ratio of the first optical data to the second optical data and comparing the parameter to a predefined threshold, the method further comprising generating the notification instructions when the parameter indicates that the contact pressure exceeds the threshold.

23. A notification-generation method for evaluating contact pressure between a wearable optical sensor and a user's skin, comprising:

(a) obtaining a first photoplethysmography (PPG) signal at a first wavelength in the range of 480-540 nm and extracting a first pulsatile component from said first PPG signal to produce first optical data;

(b) obtaining a second PPG signal at a second wavelength in the range of 650-1000 nm and extracting a second pulsatile component from said second PPG signal to produce second optical data;

(c) calculating a ratio of the first optical data to the second optical data, wherein the first optical data and second optical data each comprise a heartbeat-induced pulsatile amplitude of the respective PPG signal;

(d) comparing the calculated ratio to a predetermined pressure-indicative threshold associated with an excessive contact pressure; and (e) based on the comparison, automatically generating a notification to the user to adjust contact pressure between the sensor and the skin when the comparison indicates the contact pressure is excessive.

\*   \*   \*   \*   \*